(12) United States Patent
Taebi

(10) Patent No.: US 12,714,312 B2
(45) Date of Patent: Aug. 25, 2026

(54) VISION-BASED CARDIORESPIRATORY MONITORING

(71) Applicant: Mississippi State University, Mississippi State, MS (US)

(72) Inventor: Amirtaha Taebi, Mississippi State, MS (US)

(73) Assignee: Mississippi State University, Office of Technology Management, Mississippi State, MS (US)

( * ) Notice: Subject to any disclaimer, the term of this patent is extended or adjusted under 35 U.S.C. 154(b) by 0 days.

(21) Appl. No.: 18/779,883

(22) Filed: Jul. 22, 2024

(65) Prior Publication Data

US 2025/0025052 A1 Jan. 23, 2025

Related U.S. Application Data

(60) Provisional application No. 63/528,161, filed on Jul. 21, 2023.

(51) Int. Cl.
*A61B 5/00* (2006.01)
*A61B 5/02* (2006.01)
(Continued)

(52) U.S. Cl.
CPC .............. *A61B 5/0077* (2013.01); *A61B 5/02* (2013.01); *A61B 5/6898* (2013.01); *A61B 5/7267* (2013.01); *A61B 5/743* (2013.01); *G06T 7/0012* (2013.01); *G06T 7/11* (2017.01); *G16H 50/30* (2018.01); *G16H 50/70* (2018.01);
(Continued)

(58) Field of Classification Search
CPC ....... A61B 5/0077; A61B 5/02; A61B 5/6898; A61B 5/7267; A61B 5/473; G06T 7/11; G06T 7/0012; G06T 2207/10016; G06T 2207/20182; G06T 2207/30196; G16H 50/30; G16H 50/70
See application file for complete search history.

(56) References Cited

U.S. PATENT DOCUMENTS

2008/0221442 A1* 9/2008 Tolkowsky .......... A61B 6/5217 378/22
2016/0345832 A1* 12/2016 Pavagada Nagaraja .................... G16H 40/67
(Continued)

OTHER PUBLICATIONS

Massaroni, C., et al. "Contactless Methods for Measuring Respiratory Rate: A Review," IEEE Sensors Journal. vol. 21(11), 2021. p. 1-19 (Year: 2021).*
(Continued)

*Primary Examiner* — Sean A Frith
(74) *Attorney, Agent, or Firm* — Conley Rose, P.C.

(57) ABSTRACT

A system and method for non-invasive cardiorespiratory health assessment using a camera to capture video of a subject's chest region. The method includes tracking the motion of pixel groups in the video to construct a 3D motion map of the chest surface vibrations. The motion map is then analyzed by an artificial intelligence (AI) model to classify the subject's cardiorespiratory health status and estimate various physiological parameters. The AI model is trained on a dataset of chest vibration maps labeled with corresponding health statuses. The system can be implemented on various devices, including smartphones, and can provide real-time feedback to the user through a user interface.

20 Claims, 7 Drawing Sheets

(51) Int. Cl.

| | |
|---|---|
| ***G06T 7/00*** | (2017.01) |
| ***G06T 7/11*** | (2017.01) |
| ***G16H 50/30*** | (2018.01) |
| ***G16H 50/70*** | (2018.01) |

(52) U.S. Cl.

CPC .............. *G06T 2207/10016* (2013.01); *G06T 2207/20182* (2013.01); *G06T 2207/30196* (2013.01)

(56) References Cited

U.S. PATENT DOCUMENTS

| | | | | |
|---|---|---|---|---|
| 2017/0238805 | A1* | 8/2017 | Addison | A61B 5/1176 |
| 2019/0205694 | A1* | 7/2019 | Wang | G06V 40/165 |
| 2020/0303075 | A1* | 9/2020 | Krishna | G16H 50/30 |
| 2021/0357696 | A1* | 11/2021 | Peng | G16H 50/30 |
| 2023/0263424 | A1* | 8/2023 | Chatterjee | A61B 5/1126 600/538 |
| 2023/0270337 | A1* | 8/2023 | Petkov | A61B 5/0077 |
| 2024/0237961 | A1* | 7/2024 | Nano | A61B 5/113 |
| 2024/0285170 | A1* | 8/2024 | Wallace | G16H 10/60 |

OTHER PUBLICATIONS

Rachel M. Werner, MD, PhD, "Leading Causes of Death in the US During the COVID-19 Pandemic, Mar. 2020 to Oct. 2021," Published Online: Jun. 27, 2022. doi:10.1001/jamainternmed.2022.2273, JAMA Internal Medicine Aug. 2022 vol. 182, No. 8, pp. 883-886.

Tsao, MD., et al., "Heart Disease and Stroke Statistics—2022 Update: A Report From the American Heart Association," Circulation. 2022;145:e153-e639. DOI: 10.1161/CIR.0000000000001052, Downloaded from http://ahajournals.org Apr. 25, 2024, 487 pages.

Muthurangu, et al., "Measurement of total pulmonary arterial compliance using invasive pressure monitoring and MR flow quantification during MR-guided cardiac catheterization," Am J Physiol Heart Circ Physiol 289: H1301-H1306, 2005. First published May 6, 2005; doi:10.1152/ajpheart.00957.2004.

Taebi, et al., "Recent Advances in Seismocardiography," Vibration 2019, 2, 64-86; doi:10.3390/vibration2010005, www.mdpi.com/journal/vibration,.

Zanetti, et al., "Seismocardiography: A Technique for Recording Precordial Acceleration," [1991] Computer-Based Medical Systems@m_Proceedings of the Fourth Annual IEEE Symposium, Baltimore, MD, USA, 1991, pp. 4-9, doi: 10.1109/CBMS.1991.128936.

Taebi, et al., "Analysis of Seismocardiographic Signals Using Polynomial Chirplet Transform and Smoothed Pseudo Wigner-Ville Distribution," 2017 IEEE Signal Processing in Medicine and Biology Symposium (SPMB), Philadelphia, PA, USA, 2017, pp. 1-6, doi: 10.1109/SPMB.2017.8257022.

Inan, et al., "Ballistocardiography and Seismocardiography: A Review of Recent Advances," IEEE Journal of Biomedical and Health Informatics, vol. 19, No. 4, Jul. 2015, pp. 1414-1427.

Cook, et al., "Body Acoustics for the Non-Invasive Diagnosis of Medical Conditions," Bioengineering 2022, 9, 149. https://doi.org/10.3390/bioengineering9040149, pp. 1-17.

Sorensen, et al., "Definition of Fiducial Points in the Normal Seismocardiogram," Nature / Scientific Reports | (2018) 8:15455 | DOI:10.1038/s41598-018-33675-6, Oct. 18, 2018, pp. 1-11.

Ha, et al., "Contactless Seismocardiography via Deep Learning Radars,"MobiCom '20, Sep. 21-25, 2020, London, United Kingdom, ACM ISBN 978-1-4503-7085-1/20/09. https://doi.org/10.1145/3372224.3419982, 14 pages.

Dehkordi, et al., "Detecting Coronary Artery Disease Using Rest Seismocardiography and Gyrocardiography," Front. Physiol. 12:758727. doi: 10.3389/fphys.2021.758727, Dec. 2, 2021, 9 pages.

Salerno, et al., "Seismocardiography for Monitoring Changes in Left Ventricular Function during Ischemia*," Chest | 100 | 4 | Oct. 1991, pp. 991-993.

Hurnanen, et al., "Automated Detection of Atrial Fibrillation Based on Time—Frequency Analysis of Seismocardiograms," IEEE Journal of Biomedical and Health Informatics, vol. 21, No. 5, Sep. 2017, pp. 1233-1241.

Shandhi, et al., "Estimation of Changes in Intracardiac Hemodynamics Using Wearable Seismocardiography and Machine Learning in Patients With Heart Failure: A Feasibility Study," IEEE Transactions on Biomedical Engineering, vol. 69, No. 8, Aug. 2022, pp. 2444-2455.

Koivisto, et al., "Mechanocardiography in the Detection of Acute ST Elevation Myocardial Infarction: The Mechano-Stemi Study," Sensors 2022, 22, 4384. https://doi.org/10.3390/s22124384, 13 pages.

Zia, et al., "Enabling the assessment of trauma-induced hemorrhage via smart wearable systems," Sci. Adv. 2020; 6 : eabb1708 Jul. 22, 2020, 11 pages.

Khosrow-khavar, "Automatic and Non-Invasive Delineation of the Seismocardiogram Signal for the Estimation of Cardiac Time Intervals with Applications in Diastolic Timed Vibration and Early Stage Hemorrhage Detection," Thesis Submitted in Partial Fulfillment of the Requirements for the Degree of Doctor of Philosophy in the School of Engineering Science Faculty of Applied Sciences Simon Fraser University, 2016. 123 pages.

Buccanfuso, et al., "Collecting Heart Rate Using a High Precision, Non-Contact, Single-Point Infrared Temperature Sensor," International Conference on Social Robotics, 86-97 (Springer, 2012).

Nosrati, et al., High-Accuracy Heart Rate Variability Monitoring Using Doppler Radar Based on Gaussian Pulse Train Modeling and FTPR Algorithm, IEEE Transactions on Microwave Theory and Techniques, vol. 66, No. 1, Jan. 2018, pp. 556-567.

Gu, et al., "WiFi-based Real-time Breathing and Heart Rate Monitoring during Sleep," In 2019 IEEE Global Communications Conference (GLOBECOM), 1-6 (IEEE, 2019).

Adib, et al., "Smart Homes that Monitor Breathing and Heart Rate," Proceedings of the 33rd annual ACM conference on human factors in computing systems, 837-846 (2015).

Wu, H.-Y. et al., "Eulerian Video Magnification for Revealing Subtle Changes in the World," ACM transactions on graphics 376 (TOG) 31, 1-8 (2012).

Wadhwa, et al., "Phase-Based Video Motion Processing," ACM Transactions on Graphics, vol. 32, No. 4, Article 80, Publication Date: Jul. 2013, 10 pages.

Zhao, et al., "Remote Measurements of Heart and Respiration Rates for Telemedicine", PLoS ONE. Oct. 2013 | vol. 8 | Issue 10 | e71384 14 pages.

Chang, et al., "Learning-based Remote Photoplethysmography for Physiological Signal Feedback Control in Fitness Training," IEEE Conference on Industrial Electronics and Applications (ICIEA), 1663-1668, DOI: 10.1109/ICIEA48937.2020.9248164 (2020).

Huang, et al., "A Heart Rate Monitoring Framework for Real-World Drivers Using Remote Photoplethysmography," EEE Journal of Biomedical and Health Informatics, vol. 25, No. 5, May 2021, pp. 1397-1408, DOI: 10.1109/JBHI.2020.3026481.

Wu, et al., "Neural Network Based Luminance Variation Resistant Remote-Photoplethysmography for Driver's Heart Rate Monitoring," IEEE Access 7, 57210-57225, DOI: 10.1109/ACCESS.2019 2913664 (2019).

Yu, et al., "Noncontact Monitoring of Heart Rate and Heart Rate Variability in Geriatric Patients Using Photoplethysmography Imaging," IEEE Journal of Biomedical and Health Informatics, vol. 25, No. 5, May 2021, pp. 1781-1792.

Arppana, et al., "Real Time Heart Beat Monitoring Using Computer Vision," 2021 Seventh International conference on Bio Signals, Images, and Instrumentation (ICBSII), pp. 1-6 (IEEE, 2021).

Gibson, et al., "Non-contact heart and respiratory rate monitoring of preterm infants based on a computer vision system: a method comparison study," Pediatr. research 86, 738-741 (2019).

Sikdar, et al., "Computer-Vision-Guided Human Pulse Rate Estimation: A Review," IEEE Reviews in Biomedical Engineering, vol. 9, 2016, pp. 91-105.

(56) References Cited

OTHER PUBLICATIONS

Wang, et al., "Digital image correlation in experimental mechanics and image registration in computer vision: Similarities, differences and complements," Opt. Lasers Eng. 65, 18-27 (2015).
Lucas, et al., "An Iterative Image Registration Technique with an Application to Stereo Vision," Proceedings of Imaging Understanding Workshop, pp. 121-130 (1981).
Baker, et al., "Lucas-Kanade 20 Years on: A Unifying Framework," Int. journal computer vision 56, 221-255 (2004).
Feng, et al., "Computer vision for SHM of civil infrastructure: From dynamic response measurement to damage detection—A review," Eng. Struct. 156, 105-117 (2018).
Pan, et al., "A Real-Time QRS Detection Algorithm", IEEE Transactions on Biomedical Engineering, vol. BME-32, No. 3, Mar. 1985, pp. 230-236.
Sedghamiz, "Matlab implementation of pan tompkins ecg qrs detector. Code Available at File Exch. Site MathWorks," (2014) 6 pages . . . .
Gamage, et al., "Clustering SCG Events using Unsupervised Machine Learning," Signal Processing in Medicine and Biology, 205-233 (Springer, 2020).
Cohen, et al., "A Statistical Analysis of Morse Wavelet Coherence," IEEE Transactions on Signal Processing, vol. 58, No. 3, Mar. 2010, pp. 980-989.
Taebi, et al., "Time-Frequency Distribution of Seismocardiographic Signals: A Comparative Study," Bioengineering 4, 32 (2017), www.mdpi.com/journal/bioengineering, doi:10.3390/bioengineering4020032, 21 pages.
Zanetti, et al., "Seismocardiography: Past, Present and Future," 2013 35th annual international conference of the IEEE engineering in medicine and biology society (EMBS), Osaka, Japan, Jul. 3-7, 2013, pp. 7004-7007.
Di Rienzo, et al., "Wearable seismocardiography: Towards a beat-by-beat assessment of cardiac mechanics in ambulant subjects," Auton. Neurosci. 178, 50-59 (2013).
Azad, et al., "Spatial Distribution of Seismocardiographic Signals," Biomedical Signal Processing, 129-159 (Springer, 2021).
Matthews, et al., "The Template Update Problem," IEEE Transactions on Pattern Analysis and Machine Intelligence, vol. 26, No. 6, Jun. 2004, pp. 810-815.
"Cardiovascular diseases(CVDs)," World Health Organization, https://www.who.int/news-room/fact-sheets/detail/cardiovascular-diseases-(cvds), Jun. 11, 2021, 6 pages.
Munck, et al., "Multichannel seismocardiography: an imaging modality for investigating heart vibrations," 2020 Physiol. Meas. 41 115001, Dec. 3, 2020, https://doi.org/10.1088/1361-6579/abc0b7. 12 pages.
Lin, et al., "Identification of Location Specific Feature Points in a Cardiac Cycle Using a Novel Seismocardiogram Spectrum System," IEEE Journal of Biomedical and Health Informatics, vol. 22, No. 2, Mar. 2018, pp. 442-449.
Ashouri, et al., "Universal Pre-Ejection Period Estimation Using Seismocardiography: Quantifying the Effects of Sensor Placement and Regression Algorithms," IEEE Sens J. Feb. 15, 2018; 18(4): 1665-1674. doi:10.1109/jsen.2017.2787628.
Shirkovskiy, et al., "Airborne ultrasound surface motion camera: Application to seismocardiography," Applied Physics Letters . May 2018, DOI: 10.1063/1.5028348, 14 pages.
Rahman, et al. "Non-contact heart vibration measurement using computer vision-based seismocardiography," Scientific Reports, (2023) 13:11787, https://doi.org/10.1038/s41598-023-38607-7. 13 pages.
Wang, et al., "YOLOv7: Trainable Bag-of-Freebies Sets New State-of-the-Art for Real-Time Object Detectors," 2023 IEEE/CVF Conference on Computer Vision and Pattern Recognition (CVPR), Vancouver, BC, Canada, 2023, pp. 7464-7475, doi: 10.1109/CVPR52729.2023.00721.
Xiong, et al., "Analysis of Quadratic Surface Fitting for Subpixel Motion Extraction from Video Images," EUSIPCO 2020—28th European Signal Processing Conference, Jan. 2021, Amsterdam / Virtual, Netherlands. pp. 695-699, 10.23919/Eusipco47968.2020.9287872,hal-03129172.
Inan, PhD., et al., "Novel Wearable Seismocardiography and Machine Learning Algorithms Can Assess Clinical Status of Heart Failure Patients," Circ Heart Fail. 2018; 11:e004313. DOI: 10.1161/CIRCHEARTFAILURE.117.004313, Jan. 2018, 10 pages.
Odille, et al., "Statistical Variations of Heart Orientation in Healthy Adults," Computing in Cardiology 2017; vol. 44, ISSN: 2325-887X DOI:10.22489/CinC.2017.225-058, 4 pages.
Ioffe, et al., "Batch Normalization: Accelerating Deep Network Training by Reducing Internal Covariate Shift," Proceedings of the 32nd International Conference on Machine Learning, Lille, France, 2015. JMLR: W&CP vol. 37, 9 pages.

* cited by examiner

VISION-BASED CARDIORESPIRATORY MONITORING

CROSS-REFERENCE TO RELATED APPLICATIONS

This application claims the benefit of U.S. Provisional Patent Application Ser. No. 63/528,161, filed Jul. 21, 2023, by Amirtaha Taebi, and entitled "Vision-Based Seismocardiography," which is hereby incorporated herein by reference in its entirety for all purposes.

STATEMENT REGARDING FEDERALLY SPONSORED RESEARCH OR DEVELOPMENT

Not applicable.

TECHNICAL FIELD

The present disclosure relates generally to the field of medical devices, and more particularly to systems and methods for non-invasive vision-based assessment of cardiorespiratory health.

BACKGROUND

Heart and lung monitoring encompasses a range of technologies, each with its own strengths and weaknesses. Methods such as echocardiography and electrocardiography are used in clinical settings but involve specialized equipment and expertise. These methods may be expensive, time-consuming, and unsuitable for frequent or remote monitoring.

There has been growing interest in non-invasive and remote heart and lung monitoring techniques. Wearable devices equipped with accelerometers or photoplethysmography sensors have gained popularity for tracking heart rate and other basic metrics. However, these devices are limited in their ability to capture detailed information about heart and lung mechanics and subtle signs of underlying diseases.

Measuring chest vibrations induced by heart and lung activity has shown promise in providing a more comprehensive assessment of heart and lung health. However, such methods rely on contact sensors attached to the chest, which can be inconvenient and uncomfortable for patients. Contactless methods, such as those using lasers or radars, offer a more patient-friendly approach. However, these methods may involve expensive and complex equipment, limiting their accessibility and widespread adoption. Additionally, existing camera-based methods are limited to specific frequency bands and provide information about low-frequency heart vibrations that can mainly extract heart rate information.

SUMMARY

In an embodiment, a method comprises capturing a video of a chest surface region of a subject using a camera. The video comprises a plurality of consecutive frames. For each frame in the video, the method further comprises tracking a plurality of pixel groups within the frame. In addition, the method comprises determining a movement of each of the plurality of pixel groups between consecutive frames. Further, the method comprises constructing a motion map of the chest surface region based on the movements of the plurality of pixel groups. The motion map represents vibrations of the chest surface region.

In an embodiment, a method comprises capturing a video of a chest surface region of a subject using a camera. The method further comprises generating a chest motion map based on the captured video. Additionally, the method comprises inputting the chest motion map into an artificial intelligence (AI) model for classifying cardiorespiratory health. Further, the method comprises classifying cardiorespiratory health of the subject into a predefined cardiorespiratory category based on a classification result from the AI model The classification result indicates cardiorespiratory health status of the subject.

In an embodiment, an apparatus comprises a camera configured to capture a video of a chest surface region of a subject. The apparatus further comprises a processing unit coupled to the camera. The processing unit is configured to: track a plurality of pixel groups within each frame of the video; determine a movement of each of the plurality of pixel groups between consecutive frames; construct a motion map of the chest surface region based on the movements of the plurality of pixel groups, wherein the motion map represents vibrations of the chest surface region in three dimensions (3D); generate a chest vibration map based on the motion map; and input the chest vibration map into an AI model for cardiorespiratory health assessment.

Embodiments described herein comprise a combination of features and characteristics intended to address various shortcomings associated with certain prior devices, systems, and methods. The foregoing has outlined rather broadly the features and technical characteristics of the disclosed embodiments in order that the detailed description that follows may be better understood. The various characteristics and features described above, as well as others, will be readily apparent to those skilled in the art upon reading the following detailed description, and by referring to the accompanying drawings. It should be appreciated that the conception and the specific embodiments disclosed may be readily utilized as a basis for modifying or designing other structures for carrying out the same purposes as the disclosed embodiments. It should also be realized that such equivalent constructions do not depart from the spirit and scope of the principles disclosed herein.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION

Figure 1:
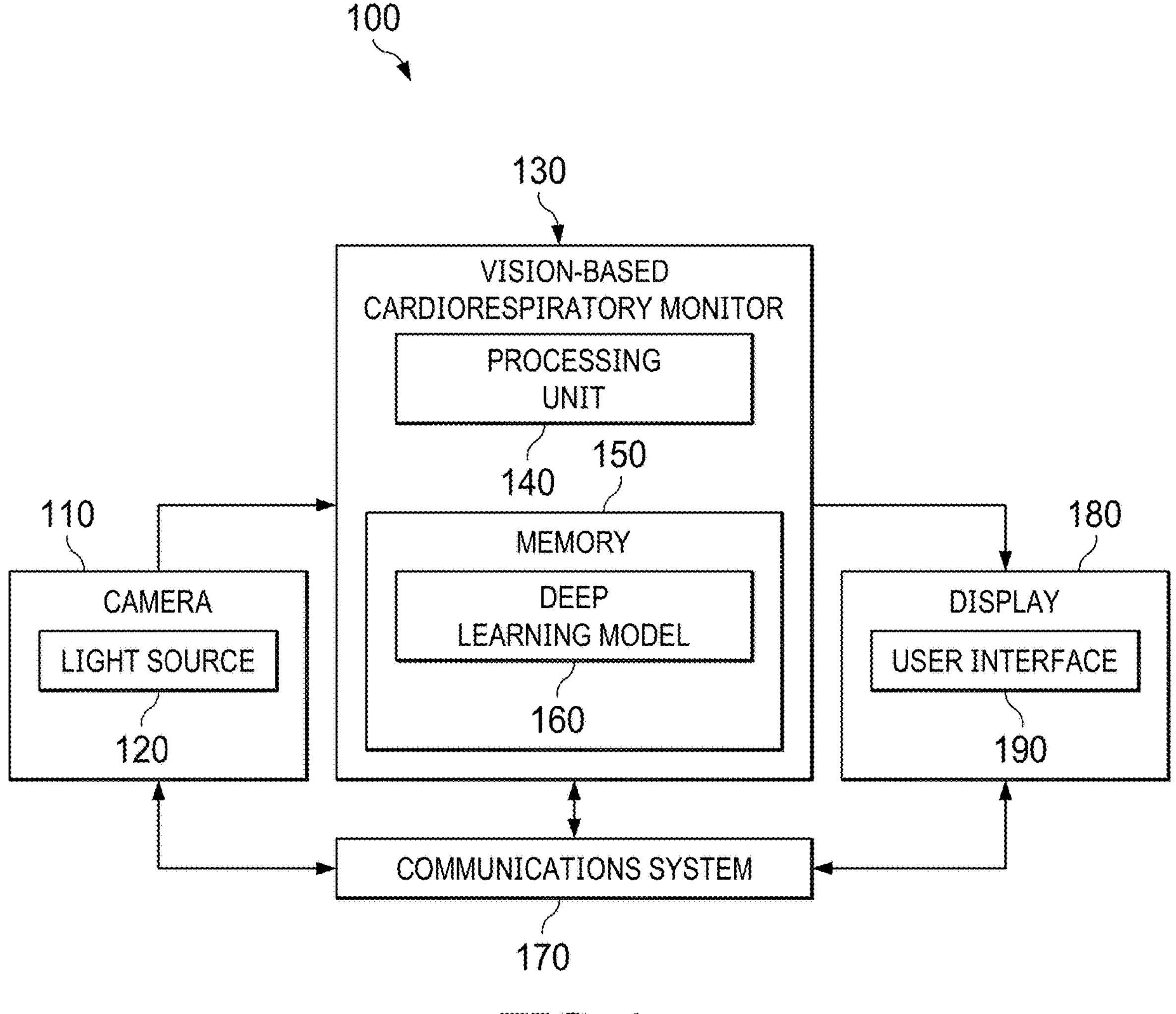
FIG. 1 is a block diagram illustrating the components and signal flow of a vision-based cardiorespiratory monitor in accordance with an embodiment of the disclosure.

It should be understood at the outset that although an illustrative implementation of one or more embodiments are provided below, the disclosed systems and/or methods may be implemented using any number of techniques, whether currently known or yet to be developed. The disclosure should in no way be limited to the illustrative implementations, drawings, and techniques illustrated below, including the exemplary designs and implementations illustrated and described herein, but may be modified within the scope of the appended claims along with their full scope of equivalents.

Thus, while several embodiments have been provided in the present disclosure, it may be understood that the disclosed systems and methods might be embodied in many other specific forms without departing from the spirit or scope of the present disclosure. The present examples are to be considered illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, components, techniques, or methods without departing from the scope of the present disclosure. Other items shown or discussed as coupled may be directly coupled or indirectly coupled or communicating through some interface, device, or intermediate component, whether electrically, mechanically, or otherwise. Other examples of changes, substitutions, and alterations are ascertainable by one skilled in the art and may be made without departing from the spirit and scope disclosed herein.

Cardiovascular diseases (CVDs) are a leading cause of mortality and morbidity worldwide, imposing an economic burden on healthcare systems. Early detection and monitoring of CVDs may aid in timely intervention and improved patient outcomes. However, diagnostic methods may rely on expensive equipment, invasive procedures, or specialized clinical settings, limiting their accessibility and frequency of use.

Diagnostic tools such as echocardiography, while informative, may be expensive, involve specialized equipment, and may necessitate visits to clinical facilities. This limits their accessibility and frequency of use, particularly for individuals in remote areas or with limited resources.

Other non-invasive methods, such as electrocardiography (ECG), primarily measure the electrical activity of the heart. While ECG provides valuable information, it may not capture subtle mechanical changes associated with early-stage CVDs.

Seismocardiography (SCG) is a non-invasive technique that measures surface vibrations of the chest wall induced by cardiac activity. These vibrations, known as seismocardiograms, contain information about cardiovascular function and can reveal subtle signs of underlying pathologies. However, SCG methods may involve attaching sensors to the chest, which can be inconvenient and uncomfortable for patients, sometimes limiting their widespread adoption.

Contactless SCG methods, which may eliminate the need for physical contact with the skin, have been proposed as a more convenient alternative. These methods may employ specialized sensors such as lasers or radars to detect chest vibrations remotely. However, such sensors may be expensive and complex, hindering their integration into portable or wearable devices.

Remote health monitoring has emerged as an approach to address these challenges. For example, the ubiquity of smartphones, equipped with high-resolution cameras and computational capabilities, may offer an opportunity to utilize non-invasive techniques for cardiovascular and respiratory assessment outside of clinical environments.

Advancements in computer vision and signal processing have paved the way for camera-based methods, where a camera is used to capture chest surface vibrations without physical contact. This approach has the potential to improve cardiovascular monitoring by allowing remote, frequent, and unobtrusive assessments of cardiac health. However, existing camera-based methods are limited to specific frequency bands and provide information about low-frequency vibrations that can mainly extract heart rate information. Additionally, camera-based methods may not fully exploit the spatiotemporal information present in video recordings of chest vibrations. For instance, these methods may only capture vibrations in one dimension, neglecting the three-dimensional (3D) nature of chest wall motion.

Disclosed here are systems and methods for vision-based cardiorespiratory monitoring. This disclosure addresses the above-discussed limitations by providing systems and methods for acquiring and analyzing video recordings of chest surface vibrations. The disclosed systems and methods may utilize computer vision algorithms to track chest surface movements in three dimensions with enhanced accuracy and precision. This allows for the extraction of a 3D vibration map of the chest surface (e.g., extraction of information about the amplitude, frequency, and direction of the vibrations across the entire chest surface), providing for a more informative representation of cardiorespiratory activity.

Moreover, the disclosed systems and methods analyze the spectrum of chest vibrations, capturing both low-frequency (e.g., 0-2 Hz) and high-frequency (e.g., above 2 Hz) components that may be relevant for detecting subtle signs of cardiovascular dysfunction. By combining 3D motion tracking with frequency analysis, the disclosed systems and method may provide a more accurate and informative assessment of cardiorespiratory health than existing vision-based methods.

The disclosed systems and methods further employ signal processing techniques to analyze the extracted vibration data and derive clinically relevant parameters. These parameters can include heart rate, heart rate variability metrics, cardiac time intervals, cardiac parameters, and the timing of cardiac events. Heart rate (HR) variability metrics include but are not limited to, standard deviation of NN intervals (SDNN), standard deviation of RR intervals (SDRR), standard deviation of the average NN intervals (SDANN), percentage of successive RR intervals that differ by more than 50 ms (pNN50), HR max, HR min, and root mean square of successive RR interval differences (RMSSD). Cardiac time interval parameters include but are not limited to, RR interval, electromechanical delay, left ventricular ejection time, pre-ejection period, isovolumic relaxation time, isovolumic contraction time, ventricular systole, ventricular diastole, and electromechanical systole. Cardiac parameters include, but are not limited to, ejection fraction, stroke volume, cardiac output, and blood pressure. Timing of cardiac events parameters include, but are not limited to, the timing of opening and closing of the aortic valve, mitral valve, pulmonary valve, and tricuspid valve. The system can also classify cardiorespiratory health status and identify potential markers of cardiovascular diseases using machine learning algorithms.

Furthermore, the disclosed systems and methods may employ machine learning algorithms to automatically analyze the extracted vibration data and derive clinically relevant parameters. This may allow for automated identification of potential markers of cardiovascular diseases, facilitating early detection and timely intervention.

FIG. 1 is a block diagram depicting some components and signal flows of a vision-based cardiorespiratory monitor system 100 according to an embodiment of the disclosure. The vision-based cardiorespiratory monitor system 100 comprises a camera 110, a light source 120, a monitor 130, a processing unit 140, a memory 150, a deep learning model 160, a communications system 170, a display 180, and a user interface (UI) 190.

The camera 110 is responsible for capturing video data of a subject's chest surface (or, more generally, chest region), which may serve as the raw input for subsequent analysis and processing. The camera 110 may be any suitable type of camera capable of recording video at a sufficient frame rate and resolution to capture the subtle movements of the chest surface induced by cardiorespiratory activity. In embodiments, the camera 110 is a camera with a frame rate of at least 30 frames per second (fps), preferably 60 fps or higher. This may allow for accurate tracking of both low-frequency and high-frequency chest vibrations, providing more comprehensive representations of cardiorespiratory functions.

The selection of an appropriate frame rate may be a consideration in vision-based cardiorespiratory monitoring. Video cameras, designed for general-purpose recording, generally have frame rates of 24 or 30 fps, which may not be sufficient to capture the full spectrum of cardiorespiratory vibrations. The frame rate of a video determines its temporal resolution, meaning how many distinct images are captured per second. In the context of cardiorespiratory monitoring, a higher frame rate generally allows for more precise tracking of the rapid vibrations of the chest surface caused by the heart and lungs. The frame rate may also dictate the maximum frequency of vibrations that can be accurately captured. According to the Nyquist-Shannon sampling theorem, the maximum detectable frequency is half the sampling rate. Therefore, a camera (e.g., the camera 110) with a frame rate of 60 fps can capture vibrations up to 30 Hz. The heart and lungs generate vibrations across a wide range of frequencies. While the dominant frequencies of the seismocardiogram (SCG) signal generally fall within the 1-20 Hz range, higher frequencies can also contain valuable information about subtle cardiac events and variations in mechanical function. By using a camera with a frame rate of at least 60 fps, the system may be able to capture a wider range of frequencies, including those that may be missed by lower frame-rate cameras. This can lead to more accurate and comprehensive assessments of cardiorespiratory health.

The camera 110 may be integrated into a smartphone, tablet, or other portable device, allowing for more accessibility and convenience in various settings. Alternatively, the camera 110 may be a standalone device, such as a webcam or a dedicated medical imaging camera. The camera 110 may be equipped with various features to enhance the quality and accuracy of the captured video data. For example, the camera 110 may have autofocus capabilities to ensure that the chest surface remains in focus throughout the recording. It may also have image stabilization to reduce motion artifacts caused by camera shake or movement of the subject. Additionally, the camera 110 may have adjustable settings for exposure, white balance, and other parameters to optimize the image quality under different lighting conditions.

In some embodiments, the camera 110 may be positioned at a fixed distance from a subject's chest surface using a tripod, stand, or other support structure. This may allow for consistent image framing and reduce variability caused by the camera 110's movement. In other embodiments, the camera 110 may be handheld or mounted on a wearable device, allowing for greater flexibility and mobility in capturing the video data. The camera 110 may also be equipped with a zoom lens to adjust the field of view and focus on specific regions of the chest. This can be useful for capturing vibrations from particular anatomical locations of interest, such as the aortic or mitral valve areas. The camera 110 may capture video data and transmit it for processing.

The specific type and model of the camera 110 may vary depending on the intended application and desired performance characteristics. However, the camera 110 is generally capable of capturing video data of sufficient quality and resolution to allow for accurate and reliable extraction of chest surface vibrations.

The light source 120 is an optional component of the vision-based cardiorespiratory monitor system 100. The light source 120 may function to provide consistent and controlled illumination of a subject's chest surface during video capture by camera 110, allowing for improved image quality and facilitating accurate tracking of chest vibrations.

In various embodiments, the light source 120 can be any suitable type of light source capable of producing illumination in the visible or near-infrared spectrum. This may include, but is not limited to, light-emitting diodes (LEDs), incandescent lamps, fluorescent lamps, or laser diodes. The choice of light source 120 may depend on factors such as power consumption, size, cost, and desired illumination characteristics.

In embodiments, the light source 120 is designed to produce uniform illumination across the chest surface, reducing shadows and variations in brightness that could interfere with the motion tracking algorithms. The light source may also be adjustable in terms of intensity and color temperature, allowing for enhancement of the illumination based on the subject's skin tone and ambient lighting conditions.

The light source 120 may be integrated into the camera 110 or positioned separately from the camera 110. In some embodiments, multiple light sources may be used to provide illumination from different angles, further reducing shadows and improving image quality. In situations where ambient lighting is sufficient, the light source 120 may not be necessary. However, in low-light conditions or when consistent illumination is desired, the light source 120 may aid in the reliability and accuracy of the vision-based cardiorespiratory monitoring system 100.

The monitor 130 may comprise processing unit 140 and memory 150. It may further comprise communications system 170. The monitor 130 may serve as an interface between the camera 110 and the processing unit 140. It may function to acquire raw video data from the camera 110 and preprocess it to prepare it for further analysis by the processing unit 140.

In various embodiments, the monitor 130 can be implemented as a dedicated hardware system, a software system running on the processing unit, or a combination of both. It may include various components and functionalities to improve video acquisition processes and allow for enhanced quality and integrity of captured data.

The monitor 130 may control the camera 110's settings, such as frame rate, resolution, exposure, and focus. These settings may be adjusted based on application necessities, ambient lighting conditions, and a subject's chest surface characteristics.

The monitor 130 may also perform initial image processing tasks, such as noise reduction, image stabilization, and color correction. These steps may help to improve the signal-to-noise ratio of the video data and enhance the accuracy of subsequent motion-tracking algorithms.

In some embodiments, the monitor 130 may include a buffer memory to temporarily store the captured video frames before they are transferred to the processing unit. This may help to smooth out any variations in data transfer rates and ensure continuous video acquisition. The monitor 130 may also communicate (via communications system 170) with the light source 120, if present, to control its intensity and illumination pattern. This may aid in improving lighting conditions for capturing clear and detailed images of the chest surface.

In addition to video acquisition and preprocessing, the monitor 130 may also perform other tasks, such as detecting the region of interest (ROI) in the video frame that corresponds to the chest surface. This may be possible using various image segmentation techniques, such as edge detection, color-based segmentation, or machine learning-based approaches.

The monitor 130 may play a role in the overall system performance by providing quality video data to the processing unit 140. The accuracy and reliability of the subsequent motion tracking, vibration analysis, and cardiorespiratory health assessment may depend on the quality of the input data provided by the monitor 130.

The processing unit 140 may be responsible for receiving the pre-processed video data from the monitor 130 and performing the computationally intensive tasks of motion tracking, vibration analysis, and cardiorespiratory health assessment. For example, the captured video data from the camera 110 may be transmitted via the monitor 130 to the processing unit 140 for further analysis. The processing unit 140 may apply various image processing algorithms, such as template matching or optical flow techniques, to track the movement of pixel groups within the video frames. This tracking information may then be used to construct a time-varying 3D motion map (i.e., 4D data) of the chest surface, which represents the time-varying vibrations induced by cardiorespiratory activity.

In various embodiments, the processing unit 140 can be implemented using a variety of hardware platforms. For example, it can be a general-purpose central processing unit (CPU), a graphics processing unit (GPU), a field-programmable gate array (FPGA), an application-specific integrated circuit (ASIC), or a combination of these. The choice of hardware may depend on factors such as computational power, energy efficiency, cost, and size constraints.

The processing unit 140 may execute software algorithms that implement the core functionalities of the system. These algorithms may include motion tracking, vibration analysis, and general cardiorespiratory health assessment. Motion tracking algorithms are algorithms for tracking the movement of pixel groups within each video frame. This can be achieved using techniques such as template matching, optical flow, block matching, or feature-based tracking. Vibration analysis may comprise algorithms for analyzing the tracked motion data to extract relevant features of the chest surface vibrations. This may involve filtering, frequency analysis, amplitude estimation, and other signal-processing techniques. General cardiorespiratory health assessment may include algorithms for classifying the subject's cardiorespiratory health status and estimating relevant parameters. This can be achieved using machine learning models, such as deep learning networks, support vector machines, or decision trees, that have been trained on a dataset of chest vibration data labeled with corresponding health conditions.

The processing unit 140 may be coupled to a memory 150, which stores the software algorithms, video data, and intermediate results of the analysis. The processing unit 140 may also interface with a deep learning model 160, which may be a specialized type of machine learning model designed to analyze patterns in data. The deep learning model 160 may be implemented using various architectures, such as convolutional neural networks (CNNs), recurrent neural networks (RNNs), or transformers.

The memory 150 may serve as a data storage repository for various elements that may be used for the vision-based cardiorespiratory system 100's operation. The memory 150 functions in conjunction with the processing unit 140 to enable the execution of algorithms, storage of captured video data, and retention of intermediate and final results from the analysis.

The memory 150 may be any suitable type of memory, such as random access memory (RAM), read-only memory (ROM), or flash memory. RAM provides read and write access and is generally used to store data that is actively being processed by the processing unit 140. This includes the video frames captured by the camera 110, intermediate results from the motion tracking and vibration analysis algorithms, and temporary variables used during computations. ROM stores permanent data that does not need to be modified, such as the firmware for the processing unit 140, boot-up instructions, and pre-trained machine learning models. Flash memory offers non-volatile storage, meaning it retains data even when the power is turned off. It can be used to store the deep learning model 160, user preferences, calibration data, and other configuration settings.

The capacity of the memory 150 may depend on the vision-based cardiorespiratory monitor system 100's requirements, such as the desired frame rate and resolution of the video, the complexity of the algorithms, and the amount of data to be stored. In general, the memory 150 should be sufficient to accommodate the video data captured during a monitoring session, as well as the intermediate and final results of the analysis.

The deep learning model 160 may utilize artificial intelligence (AI) techniques to analyze the complex patterns and features extracted from the chest vibration maps generated by the processing unit 140. By learning from vast amounts of data, the deep learning model 160 may allow the system to more accurately classify cardiorespiratory health status, estimate various physiological parameters, and detect potential abnormalities.

The deep learning model 160 can be implemented using various architectures, each with its own strengths and suitability for different tasks. Some architectures that may be employed include convolutional neural networks (CNNs), recurrent neural networks (RNNs), long short-term memory (LSTM) networks, large language models (LLMs), or transformers. CNNs may be well-suited for image and video analysis tasks, making them effective at processing the spatiotemporal patterns in chest vibration maps. They can automatically learn hierarchical features from the data, capturing subtle details that may be relevant for health assessment. RNNs generally excel at handling sequential data, making them suitable for analyzing the temporal evolution of chest vibrations. They can model dependencies between consecutive frames and capture dynamic changes in cardiorespiratory activity. LSTM networks refer to a type of RNN that is particularly good at capturing long-term dependencies in sequential data. Transformers have gained prominence in natural language processing and computer vision tasks. They can capture long-range dependencies and contextual relationships in the data, which may be beneficial for understanding the complex interplay of various physiological factors in cardiorespiratory health. The specific architecture and implementation of the deep learning model 160 may depend on the desired functionality, available computational resources, and the nature of training data. The deep learning model 160 may consist of multiple layers, each performing specific operations such as feature extraction, dimension reduction, or classification.

The deep learning model 160 may be trained using a dataset of chest vibration maps labeled with corresponding cardiorespiratory health conditions or parameters. This training process may involve adjusting the deep learning model 160's parameters to optimize its ability to accurately classify health status and estimate relevant parameters. The deep learning model 160 may be validated on a separate dataset to ensure its generalizability and performance on unseen data.

The deep learning model 160 may perform several functions within the system, including classification, parameter estimation, and anomaly detection. The deep learning model 160 may classify a subject's cardiorespiratory health into predefined categories, such as "healthy," "abnormal," or specific disease conditions. Further, the deep learning model 160 may estimate various cardiorespiratory parameters, such as heart rate, heart rate variability, cardiac time intervals, cardiac output, and the timing of cardiac events. Additionally, the deep learning model 160 may identify unusual patterns or deviations from normal physiological behavior, potentially indicating early signs of disease or deterioration in health status.

The communications system 170 may be an optional component of the vision-based cardiorespiratory monitor system 100. The communications system 170 may facilitate the transmission and reception of data between the system and external devices or networks. This may allow a range of functionalities, including remote monitoring, data sharing, and integration with other healthcare systems.

The communications system 170 may support various communication protocols and technologies, including wireless communication, wired communication, or near-field communication (NFC). Wireless communication may include Wi-Fi, Bluetooth, cellular networks (e.g., 4G, 5G), and other wireless standards. Wireless communication allows for flexible and convenient data transfer without the need for physical cables. Wired communication may include Ethernet, USB, and other wired interfaces. Wired communication can provide higher bandwidth and reliability for large data transfers or real-time monitoring applications. NFC generally allows for short-range communication between devices in close proximity. This can be used for secure pairing with wearable devices or transferring data to a smartphone for further analysis.

The communications system 170 may perform several functions, including data transmission, data reception, remote monitoring, or software updates. For example, the communications system 170 may transmit the processed data from the monitor 130, such as the chest vibration maps, cardiorespiratory health classification results, and estimated parameters, to external devices (e.g., the UI 190) or cloud-based platforms for storage, analysis, and sharing with healthcare providers. Additionally, the communications system 170 may receive data from external devices, such as wearable sensors or other medical devices, to augment the information obtained from the vision-based monitor. This can provide a more comprehensive view of the patient's health status and allow for more accurate diagnoses and treatment decisions. Further, the communications system 170 may facilitate instantaneous monitoring of a patient's cardiorespiratory health, for example, by transmitting data to a remote server or healthcare provider's platform. This may allow for continuous assessment and early detection of potential abnormalities, even when the patient is not physically present in a clinical setting. The communications system 170 may also receive software updates and patches to improve the system's functionality, security, and performance.

The display 180 is a visual output component of the vision-based cardiorespiratory monitor system 100. The display 180's function is to present information to the user, including feedback during monitoring, results of the analysis, and other relevant data or instructions.

The display 180 can be implemented using various technologies, each with its own advantages and trade-offs. For example, the display 180 may be a liquid crystal display (LCD). LCDs are common in portable devices due to their low power consumption and thin form factor. They can offer color reproduction and resolution suitable for displaying detailed visualizations. Alternatively, display 180 may be an organic light-emitting diode (OLED) display. OLEDs generally provide contrast and color accuracy, as well as wide viewing angles. They can also be thinner and more flexible than LCDs, which can be advantageous for wearable devices. Further, display 180 may be implemented as a touchscreen display. Touchscreen displays may allow for direct interaction with the UI 190, improving navigation and control of the vision-based cardiorespiratory monitor system 130.

The display 180 may serve various functions in the vision-based cardiorespiratory monitor system 100. It may provide instantaneous feedback—for example, during the monitoring process, the display 180 may show a live video feed of the subject's chest, along with visual cues to guide the user in positioning the camera 110 to improve capture conditions. Once analysis is complete, the display 110 may present the results in a manner that improves user comprehension. Such visualization of results may include time-varying 3D chest motion maps, cardiorespiratory health classifications, or estimated parameters. A time-varying 3D chest motion map is a visualization of the chest vibrations, which may highlight areas of interest and potential abnormalities. Cardiorespiratory health classifications may comprise one or more indications of the subject's health status (e.g., healthy, abnormal, or specific conditions) based on the AI model's (e.g., deep learning model 160) analysis. Estimated parameters may include numerical values or graphical representations of estimated cardiorespiratory parameters, such as heart rate, heart rate variability, and cardiac time intervals. The display 180 may also serve as a platform for the UI 190, presenting menus, buttons, and other interactive elements that allow users to control the vision-based cardiorespiratory system 100 and access its various functions.

The display 180 may be designed to enhance readability, brightness and contrast, color accuracy, and viewing angle. The display 180 may be large enough and have sufficient resolution to allow legible text, numbers, and graphics in different lighting conditions. The display 180 may have adjustable brightness and contrast settings to accommodate various ambient lighting conditions and user preferences. If display 180 shows color images or visualizations, more accurate color reproduction may allow for conveying information effectively. The display 180 may have a wide viewing angle to allow for visible content in different positions.

The UI 190 may allow for interaction between a user and the monitor 130 in the vision-based cardiorespiratory monitor system 100. The UI 190 may provide an interface that allows the user to initiate and control the monitoring process, view the results of the analysis, and access additional features or settings.

The UI 190 may be implemented in various forms, depending on the specific device and context of use. Some implementations may include mobile applications (apps), web interfaces, or embedded displays. A mobile app may be a dedicated application running on a smartphone or tablet, offering a touch-based interface with intuitive navigation and visualization tools. A web-based interface may be accessible through a browser, providing flexibility for use on various devices with internet connectivity. A built-in display on the monitor 130 device itself may offer a direct interface for basic interactions and visualization.

The UI 190 may provide a range of functionalities to facilitate user interaction and enhance the overall user experience. Some functionalities may include initiating and controlling monitoring, displaying instantaneous feedback, visualizing results, or accessing additional features. In terms of initiating and controlling monitoring, the UI 190 may allow a user to start and stop the monitoring process, adjust camera settings (e.g., frame rate, resolution, zoom), and select specific regions of interest on the chest surface. In terms of displaying instantaneous feedback, the UI 190 may provide visual feedback to the user during the monitoring process, such as a live video feed of the chest surface, progress indicators, and notifications. In terms of visualizing results, the UI 190 may present the results of the analysis on a display (e.g., display 180) in visual representations of the chest motion map, graphs and charts of the extracted parameters, and indications of the classified cardiorespiratory health status. Further, the UI 190 may provide access to additional features, such as historical data tracking, personalized health reports, educational resources, and the ability to share data with healthcare providers.

The design of the UI 190 may aid in enhancing user experience. Some design considerations may include intuitive navigation, visually appealing design, accessibility, or responsiveness. For example, the UI 190 may be designed to be navigable with instructions for performing different tasks. Further, the UI 190 may utilize colors, fonts, and layouts to enhance readability and comprehension. Additionally, the UI 190 may be designed to be accessible to users with diverse abilities, including those with visual or motor impairments. Also, the UI 190 may be responsive to user input, providing improved feedback and reduced delays.

Figure 2:
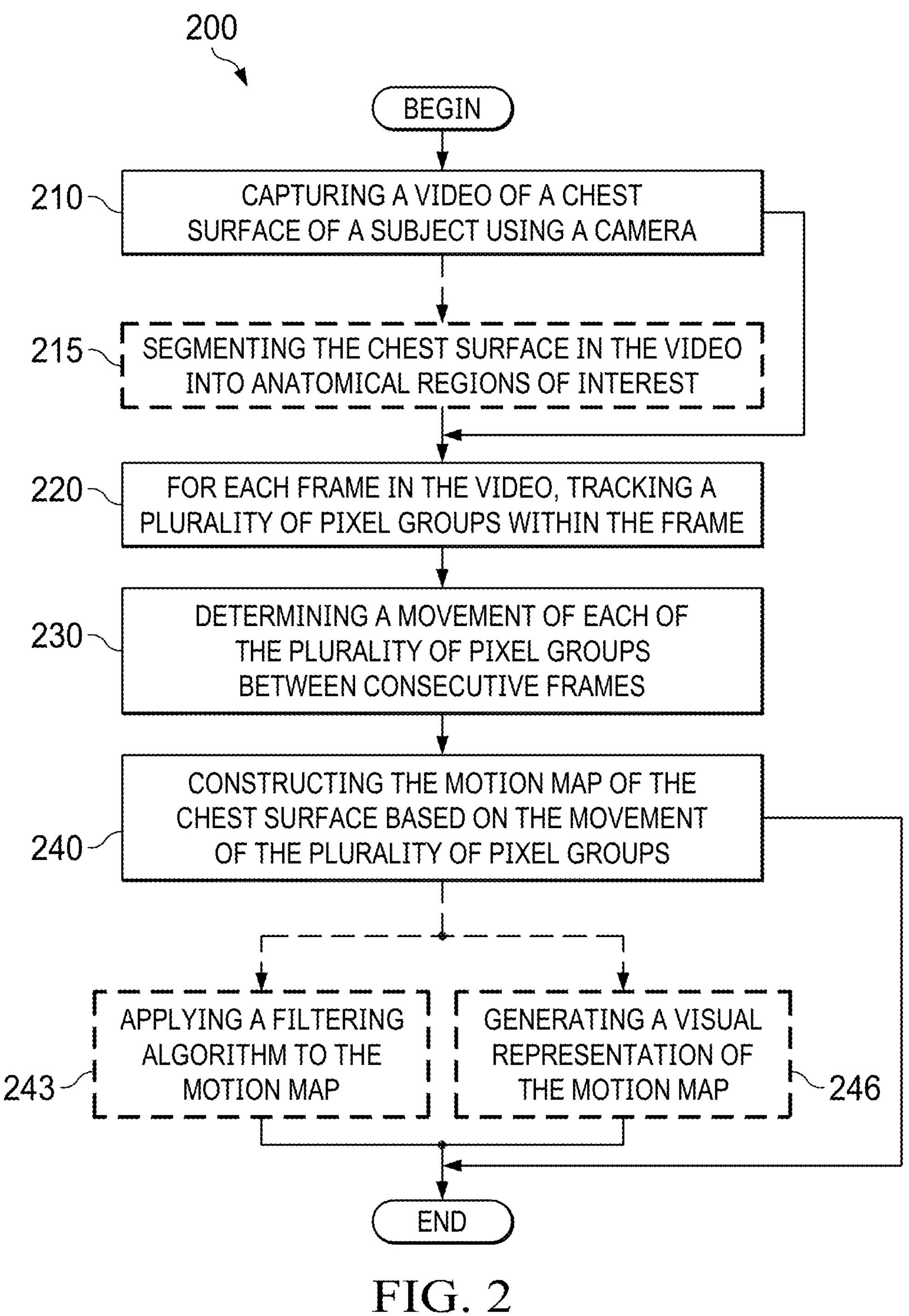
FIG. 2 is a flowchart of a method for acquiring a motion map of chest surface vibrations in accordance with an embodiment of the disclosure.

FIG. 2 illustrates a method 200 for acquiring a motion map of chest surface vibrations according to an embodiment of the disclosure. The method 200 may be implemented non-invasively and may provide an estimation of parameters (e.g., cardiac output). The motion map of chest surface vibrations may be a dynamic 3D vibration map.

At step 210, the method 200 includes capturing a video of a chest surface of a subject using a camera. The video of the chest generally includes a plurality of consecutive frames (e.g., a sequence of still images). Step 210 may be followed by step 215, but may more generally be followed by step 220—both discussed infra.

The camera can be any suitable imaging device capable of recording video, including but not limited to smartphone cameras, webcams, digital cameras, or specialized medical imaging cameras. The camera may capture frames at a specific rate, generally measured in frames per second (fps). The frame rate may aid in capturing the subtle and rapid vibrations of the chest surface caused by cardiac and respiratory activity. A higher frame rate generally allows for more precise tracking of these vibrations. The resolution of the video refers to the number of pixels in each frame. Higher resolution provides more detailed information about the chest surface, allowing for finer-grained analysis of the vibrations. The duration of the video capture can vary depending on the specific application and the desired level of detail in the analysis. A longer video duration may allow for capturing a wider range of cardiorespiratory events and variations over time.

The video is more generally focused on the chest surface, as this is the area where the vibrations of interest are most prominent. However, the exact framing and field of view can be adjusted based on the specific goals of the monitoring session. In some cases, the skin may be prepared before recording to enhance the visibility of surface features and improve motion tracing accuracy. This may involve cleaning the skin, applying a light powder, or using markers to highlight specific anatomical landmarks. Additionally, the video may be captured while the chest surface is not directly exposed (e.g., while a subject is clothed). That is, video capture in the method 200 (and relatedly, the method 300 discussed below) may be performed on a chest region with clothing present.

Capturing a plurality of consecutive frames may allow for the analysis of the temporal dynamics of the chest vibrations, revealing patterns and changes that may be indicative of underlying cardiorespiratory conditions. By analyzing the changes in pixel positions or intensities between consecutive frames, the method 200 may track the motion of the chest surface and extract the underlying vibrations. The frame rate of the video may determine the sampling rate of the vibration signal. A higher frame rate generally allows for capturing higher-frequency components of the vibrations, which may be relevant for certain diagnostic purposes.

At step 215, the method 200 may include segmenting the chest surface in the video into anatomical regions of interest. Step 215 may be considered an optional refinement step in the method 200. More generally, step 210 may be followed by step 220, discussed below.

The chest surface can be divided into distinct anatomical regions of interest (ROIs) that correspond to specific underlying structures, such as the heart chambers, valves, and major blood vessels. These regions may be considered of interest because the vibrations originating from these structures can provide diagnostic information about cardiovascular health. The chest surface can be divided into distinct anatomical regions that correspond to specific underlying structures, such as the heart chambers, valves, and major blood vessels.

The chest surface is not a uniform structure, and different regions may exhibit distinct patterns of vibration due to the underlying anatomy and physiology. By segmenting the chest surface into anatomical ROIs, the method 200 can leverage this spatial heterogeneity to extract more meaningful and diagnostically relevant information.

Various image processing and computer vision techniques can be employed to segment the chest surface into ROIs. These techniques may include edge detection, color-based segmentation, texture analysis, or machine learning-based segmentation. Edge detection generally involves identifying boundaries between different regions based on changes in pixel intensity or color. Color-based segmentation generally involves separating regions based on their color or intensity values. Texture analysis generally involves analyzing the texture patterns of the skin to distinguish between different regions. Machine learning-based segmentation generally involves utilizing trained machine-learning models to automatically identify and delineate anatomical regions based on learned patterns.

Tracking pixel groups within ROIs may involve various types of analysis. By segmenting the chest surface into ROIs, the method 200 may focus its motion-tracking efforts on the specific regions that are most relevant for cardiorespiratory assessment (e.g., via the camera 110). This can improve the accuracy and efficiency of the analysis by reducing the computational load and minimizing the impact of noise or artifacts from irrelevant areas. Furthermore, segmenting the chest surface may also allow for region-specific analysis of the vibrations. For example, the component parts discussed in method 200 may be able to track the motion of pixel groups within the aortic valve region to assess aortic valve function or focus on the left ventricular region to evaluate left ventricular contractility.

By analyzing vibrations from specific anatomical locations, the method 200 may identify variations that may be indicative of specific cardiovascular conditions. This can lead to more accurate and early detection of diseases.

Step 215 is described as occurring before tracking the plurality of pixel groups. This suggests that the segmentation is performed as a preprocessing step prior to the main motion-tracking algorithm. However, in some embodiments, the segmentation and tracking steps may be performed iteratively or in parallel to improve analysis.

At step 220, the method 200 may include tracking a plurality of pixel groups within the frame. The tracking at step 220 is performed for each frame in the video, emphasizing that the tracking process is performed iteratively. This frame-by-frame analysis may allow the method 200 to capture the temporal evolution of the chest movements and construct a dynamic representation of the vibrations. The frame rate of the video may determine the temporal resolution of the tracking process. A higher frame rate generally allows for more frequent tracking of the pixel groups, which may result in a more detailed and accurate representation of the chest motion.

The method 200 focuses on groups or clusters of pixels. This may be referred to as block matching or patch tracking. By tracking groups of pixels, the method 200 may capture larger-scale movements and reduce the impact of noise or artifacts that may affect individual pixels. Further, the pixel groups can be selected based on various criteria, such as their location, texture, or intensity. For example, the method 200 may focus on pixel groups that correspond to anatomical landmarks, regions of high contrast, or areas with distinct motion patterns. Additionally, tracking groups of pixels can be more computationally efficient than tracking individual pixels, as it reduces the number of elements that may be analyzed and tracked.

Tracking algorithms may include template matching, optical flow, block matching, or feature-based tracking. Template matching involves comparing a predefined template image (representing a region of interest within a pixel group) against a search area in subsequent frames of the video. The location in the search area where the template best matches the image indicates the new position of the pixel group. Various similarity measures can be used to assess the degree of match between the template and the search area. Some measures include Sum of Squared Differences (SSD), Cross-Correlation (CC), and Normalized Cross-Correlation (NCC). SSD generally calculates the squared difference between corresponding pixel intensities in the template and search area, summing the results. Lower SSD values generally indicate better matches. CC generally measures the similarity between the template and search area by computing their cross-correlation function. Higher CC values generally indicate better matches. NCC is a normalized version of CC that is less sensitive to changes in illumination.

Within the context of template matching, different search strategies can be employed to efficiently locate the best match within the search area. These strategies may include exhaustive search, hierarchical search, and Fast Fourier Transform (FFT)-based search. An extensive search may compare the template to every possible location in the search area. This may be computationally intensive, but it improves the chances of finding the best match. A hierarchical search generally starts with a coarse search at a lower resolution and gradually refines the search at higher resolutions. This can significantly reduce the computational cost. A FFT-based search generally utilizes the properties of the Fourier transform to accelerate the search process.

Template matching can handle moderate amounts of deformation or changes in the appearance of the pixel group between frames. This is notable in the context of chest surface vibrations, as the shape and appearance of the chest may change slightly due to breathing or other movements. Template matching also may allow for tracking specific features or landmarks on the chest surface, such as anatomical markers or regions of interest. This can provide beneficial information about the localized motion of the chest wall. Template matching is generally straightforward to implement and can be computationally efficient, especially when combined with appropriate search strategies.

Alternatively, the optical flow technique estimates the motion of pixels between frames by analyzing the changes in image intensity. The Farneback optical flow algorithm is a specific type of optical flow algorithm that is known for its robustness and accuracy. This technique, while related to general optical flow methods, may offer advantages and nuances that may be useful in the context of vision-based cardiorespiratory monitoring.

The Farneback algorithm estimates the motion of pixels between consecutive frames by analyzing the changes in image intensity. It assumes that the intensity of a pixel remains relatively constant as it moves from one frame to the next. A feature of the Farneback algorithm is its use of polynomial expansion to approximate the local image intensity around each pixel. This generally allows for capturing more complex motion patterns, including translations, rotations, and small deformations, compared to simpler methods like block matching. The Farneback algorithm is a dense optical flow method, meaning it estimates the motion of every pixel in the image, not just a sparse set of features. This generally provides a more comprehensive and detailed representation of the chest surface motion. The Farneback algorithm is known for its robustness to noise and variations in illumination. This may be useful in real-world scenarios where the lighting conditions and the appearance of the chest surface may not be thoroughly controlled.

In the context of vision-based cardiorespiratory monitoring, the Farneback algorithm may offer several advantages over other tracking methods. The Farneback algorithm can provide highly accurate motion estimates, especially for small and subtle movements like those associated with chest vibrations. The dense nature of the algorithm generally allows for capturing fine-grained details of the motion field, which can be useful in identifying subtle variations in cardiorespiratory activity. The algorithm's robustness to noise and illumination changes makes it suitable for real-world applications where these factors may vary.

Further, block-matching algorithms divide each frame into small blocks or patches and search for the matching block in the subsequent frame. Displacements between the two blocks may be used to estimate the motion of the pixel group. Additionally, feature-based tracking may involve identifying and tracking distinctive features within the pixel group, such as corners or edges. The movement of these features can then be used to estimate the overall motion of the pixel group.

By tracking a plurality of pixel groups in each frame of the video, the method 200 may be able to capture the 3D motion of the chest surface and extract the underlying vibrations with spatial and temporal resolution. This information may then be used to construct a motion or vibration map that serves as a basis for subsequent analysis and cardiorespiratory health assessment.

At step 230, the method 200 may include determining a movement of each of the plurality of pixel groups between consecutive frames. Step 230 is where the raw video data captured by the camera is transformed into information about the motion or vibration of the chest surface.

An objective of step 230 is to quantify a movement of each tracked pixel group between consecutive frames in the video. This movement is generally represented as a displacement vector, which has both magnitude (distance traveled) and direction. Various algorithms and techniques can be used to estimate the motion of pixel groups, such as optical flow, block matching, or feature-based tracking, as discussed above.

In some embodiments, the method 200 may utilize additional information, such as depth data from a depth camera or stereo vision algorithms, to estimate the 3D motion of the pixel groups. This may allow for a more comprehensive understanding of the chest surface movements, including both in-plane and out-of-plane displacements.

In other embodiments, multiple cameras may be used to capture the chest surface from different angles. This multi-view information can be combined to reconstruct the 3D motion of the pixel groups with greater accuracy and robustness.

The ability to accurately determine the movement of pixel groups may aid in understanding the dynamics of the chest surface vibrations. These vibrations are not uniform across the entire chest but rather vary in amplitude, frequency, and direction depending on the underlying anatomical structures and physiological processes. By tracking the movement of pixel groups in three dimensions and over time, the method 200 can create a map of the chest surface vibrations. This map can then be used to extract relevant features, classify cardiorespiratory health status, estimate physiological parameters, and potentially detect subtle signs of underlying conditions.

At step 240, the method 200 may include constructing the motion map of the chest surface based on the movement of the plurality of pixel groups. Step 240 may be the culmination of the motion tracking process, transforming the raw pixel group movements into a structured representation of the chest surface vibrations. This motion map may serve as an input for subsequent analysis and interpretation.

Motion map construction may involve aggregation of pixel group movements, spatial representation, and visualization. The motion map may be constructed by aggregating the displacement vectors calculated for each pixel group across the entire video sequence. This creates a representation of how different regions of the chest surface move over time.

The chest motion map can be represented in various formats, depending on the specific implementation and the requirements of the subsequent analysis. For example, the motion map can be visualized as a heatmap, where the color or intensity of each pixel indicates the amplitude of the vibration at that location. Alternatively, the motion map can be visualized as a 3D vector field, where arrows indicate the direction and magnitude of the motion vectors at different points on the chest surface. Additionally, the motion map can be represented as a matrix, where each element corresponds to the displacement vector of a specific point. This matrix can then be processed using mathematical and signal-processing techniques to extract relevant features and parameters. Additionally, the motion map can be represented as a time series of 2D or 3D images, where each image corresponds to a specific time point in the video. This may allow for analyzing the temporal evolution of the chest surface vibrations.

The motion map may be a 2D or 3D array, where each element represents the displacement of a pixel group at a specific location on the chest surface. The dimensions of the map correspond to the spatial resolution of the video, while the values within the map represent the magnitude and direction of the movements. By tracking pixel group movements in three dimensions (along the x, y, and z axes), the method 200 may capture a more complete and accurate representation of the chest surface vibrations. This may be useful because the heart's mechanical activity induces axial and rotational vibrations that are not confined to a single plane.

3D tracking may involve the acquisition of depth information, which can be obtained through various techniques such as stereo vision, structured light, or time-of-flight (ToF) sensors. Stereo vision generally involves using two or more cameras to triangulate the position of points in 3D space. Structured light generally projects a pattern of light onto the chest surface and analyzes the deformation of the pattern to infer depth. ToF sensors generally measure the time it takes for light to travel from the sensor to the chest surface and back, calculating the distance based on the speed of light.

Several algorithms can be employed for 3D motion tracking, including 3D optical flow, Structure from Motion (SfM), and Simultaneous Localization and Mapping (SLAM). 3D optical flow generally extends traditional 2D optical flow algorithms to estimate motion in all three dimensions. SfM generally reconstructs the 3D structure of the chest surface and tracks its movement over time. SLAM generally combines motion tracking with real-time mapping of the environment, allowing improved tracking even in dynamic scenarios.

The 3D motion map is a volumetric representation of the chest surface vibrations, where each element in the 3D grid represents the displacement vector of a pixel group in 3D space. This map can be visualized as a 3D vector field, where arrows indicate the direction and magnitude of the movements at different locations on the chest surface. The 3D motion map captures information about the dynamics of the chest surface vibrations, including their amplitude, frequency, direction, and spatial distribution. This information can be used to derive a variety of clinically relevant parameters, such as cardiac output, ejection fraction, and valve timing.

The specific implementation of 3D motion tracking can vary depending on the available hardware and desired level of accuracy. The method 200 is not limited to any particular 3D tracking algorithm or depth sensing technology, allowing for flexibility and adaptation to different scenarios and use cases.

The motion map is not merely a visualization of pixel movements; it is a representation of the underlying vibrations of the chest surface. These vibrations are caused by the mechanical activity of the heart and lungs, and their patterns and characteristics can provide insights into cardiorespiratory health. The motion map generally serves as a source of information for feature extraction. Various features, such as the amplitude, frequency, and spatial distribution of the vibrations, can be extracted from the motion map and used for subsequent analysis. The motion map can be directly input into a machine learning model, such as the deep learning model 160, for cardiorespiratory health assessment. The model can then use the patterns and features in the motion map to classify health status, estimate parameters, and detect potential abnormalities. Thus, motion map interpretation may involve the representation of vibrations, feature extraction, and input to an AI model.

In some embodiments, the motion map can be further processed and refined to enhance its utility. For example, filtering techniques can be applied to reduce noise or artifacts, and segmentation algorithms can be used to isolate specific regions of interest. In other embodiments, the motion map can be used in conjunction with other physiological signals, such as electrocardiograms (ECGs) or respiratory signals, to provide a more comprehensive assessment of cardiorespiratory health. Further, the motion map can be stored and analyzed over time to track changes and trends in cardiorespiratory function, enabling early detection of potential abnormalities and personalized health management.

The motion map may be seen as an intermediate representation that bridges the gap between the raw video data and the clinically relevant information. It may condense the vast amount of information contained in the video into a structured format that is amenable to further analysis and interpretation. By representing the chest surface vibrations in a spatial and temporal context, the motion map may allow for a comprehensive understanding of the complex dynamics of cardiorespiratory activity. This information can then be used to develop personalized health assessments, monitor disease progression, and guide treatment decisions.

After step 240, the method 200 may end. Alternatively, step 240 may be followed by step 243 and/or step 246 before the method 200 concludes.

At step 243, the method 200 may include applying a filtering algorithm to the motion map. As noted above, step 243 may be an optional step in the method 200 and may be done separately from or in conjunction with step 246 (discussed below).

Step 243 may aid in addressing the challenge of noise in video-based motion tracking. Noise can arise from various sources, such as camera sensor imperfections, variations in lighting, or subtle movements of the subject unrelated to cardiorespiratory activity. Filtering is a step that may enhance the signal-to-noise ratio and ensure the accuracy and reliability of the extracted vibration information.

Noise is a challenge in measurement systems, and vision-based motion tracking is no exception. The camera sensor, environmental factors, and subject movement can all introduce noise into the video data. This noise can obscure the subtle vibrations of the chest surface and hinder the accurate estimation of cardiorespiratory parameters. A goal of filtering is to remove or attenuate unwanted noise components from the motion map while preserving the true signal of interest, which are the chest surface vibrations caused by cardiac and respiratory activity.

By applying appropriate filtering algorithms, the method 200 may reduce the impact of noise and enhance the quality of the motion map. This may lead to more reliable extraction of cardiorespiratory features, improved classification accuracy, and more accurate estimation of physiological parameters. Various types of filtering algorithms can be employed, including low-pass filters, high-pass filters, band-pass filters, and adaptive filters. Low-pass filters generally allow low-frequency components of the signal to pass through while attenuating higher frequencies, effectively smoothing out the motion map and removing high-frequency noise. High-pass filters generally allow high-frequency components to pass through while attenuating lower frequencies, which may be useful for isolating the cardiac-induced vibrations from slower respiratory movements. Band-pass filters generally allow a range of frequencies to pass through, targeting the frequency bands relevant to cardiorespiratory activity. Adaptive filters generally adjust their filtering characteristics based on the input signal, providing greater flexibility and adaptability to varying noise levels. The filtering algorithm can be implemented in various ways, such as using finite impulse response (FIR) or infinite impulse response (IIR) filters, wavelet transforms, or other signal processing techniques.

Filtering is a technique in signal processing and has been widely used in various fields, including medical imaging, audio processing, and communications. The choice of filtering algorithm and parameters may depend on the characteristics of the noise, the nature of the signal of interest, and the desired level of noise reduction. For example, the selection of filtering parameters may include cutoff frequency and filter order. The cutoff frequency determines the boundary between the frequencies that are passed through and those that are attenuated. The choice of cutoff frequency depends on the specific application and the desired balance between noise reduction and signal preservation. The filter order affects the steepness of the filter's roll-off and its ability to discriminate between different frequencies. Higher-order filters can provide more precise control over the frequency response but may introduce phase distortion.

At step 246, the method 200 may include generating a visual representation of the motion map. As noted above, step 246 may be an optional step in the method 200 and may be done separately from or in conjunction with step 243 (discussed above).

Step 246 in the method 200 involves transforming the numerical data contained in the motion map into a visual format that is more easily interpretable by humans. The visual representation may provide a way to grasp the overall patterns of chest surface vibrations and identify potential areas of interest or concern.

The motion map can be visually represented in various ways, such as heat maps, vector fields, 3D surface plots, or animations—each offering potentially different perspectives and insights. A heatmap uses color gradients to represent the amplitude of the vibrations at different locations on the chest surface. Warmer colors (e.g., red, orange) indicate regions of higher amplitude, while cooler colors (e.g., blue, green) represent lower amplitude. A vector field uses arrows to depict the direction and magnitude of the movements at each point on the chest surface. The length and orientation of the arrows correspond to the magnitude and direction of the displacement vectors in the motion map. A 3D surface plot visualizes the motion map as a three-dimensional surface, where the height of the surface represents the amplitude of the vibrations at different locations. This can provide a more intuitive understanding of the spatial distribution of the vibrations. An animation of the motion map over time can reveal the dynamic nature of the chest surface vibrations, showing how they evolve and change throughout the cardiac cycle. These motion maps can be magnified for more enhanced visualizations. For example, the displacement vectors can be multiplied by a constant factor.

The visual representation of the motion map offers several benefits, such as intuitive interpretation, qualitative assessment, and a tool for communication. The human visual system is generally suited for recognizing patterns and anomalies in visual data. By converting the numerical motion map into a visual representation, the method 200 may make it easier for users, including clinicians and researchers, to interpret the data and identify potential areas of interest. The visual representation may also allow for a qualitative assessment of the overall pattern of chest vibrations. This may be useful for identifying abnormalities or asymmetries that may warrant further investigation. Additionally, the visual representation can serve as a communication tool between healthcare providers and patients. It can help to explain the underlying physiological processes and visualize the impact of different interventions or treatments.

Visual representations are a practice in many fields, including medicine, engineering, and data analysis. Visualizations can distill complex data into a more accessible and understandable form, facilitating decision-making and communication. In the context of cardiorespiratory monitoring, the visual representation of the motion map may provide a tool for clinicians and researchers to gain insights into the underlying physiological processes. It can aid in the diagnosis of cardiovascular and respiratory conditions, the monitoring of disease progression, and the assessment of treatment efficacy. The choice of visual representation may depend on the specific application and the preferences of the user. The method 200 may offer different visualization options, allowing the user to select the one that suits their requests and expertise.

Figure 3:
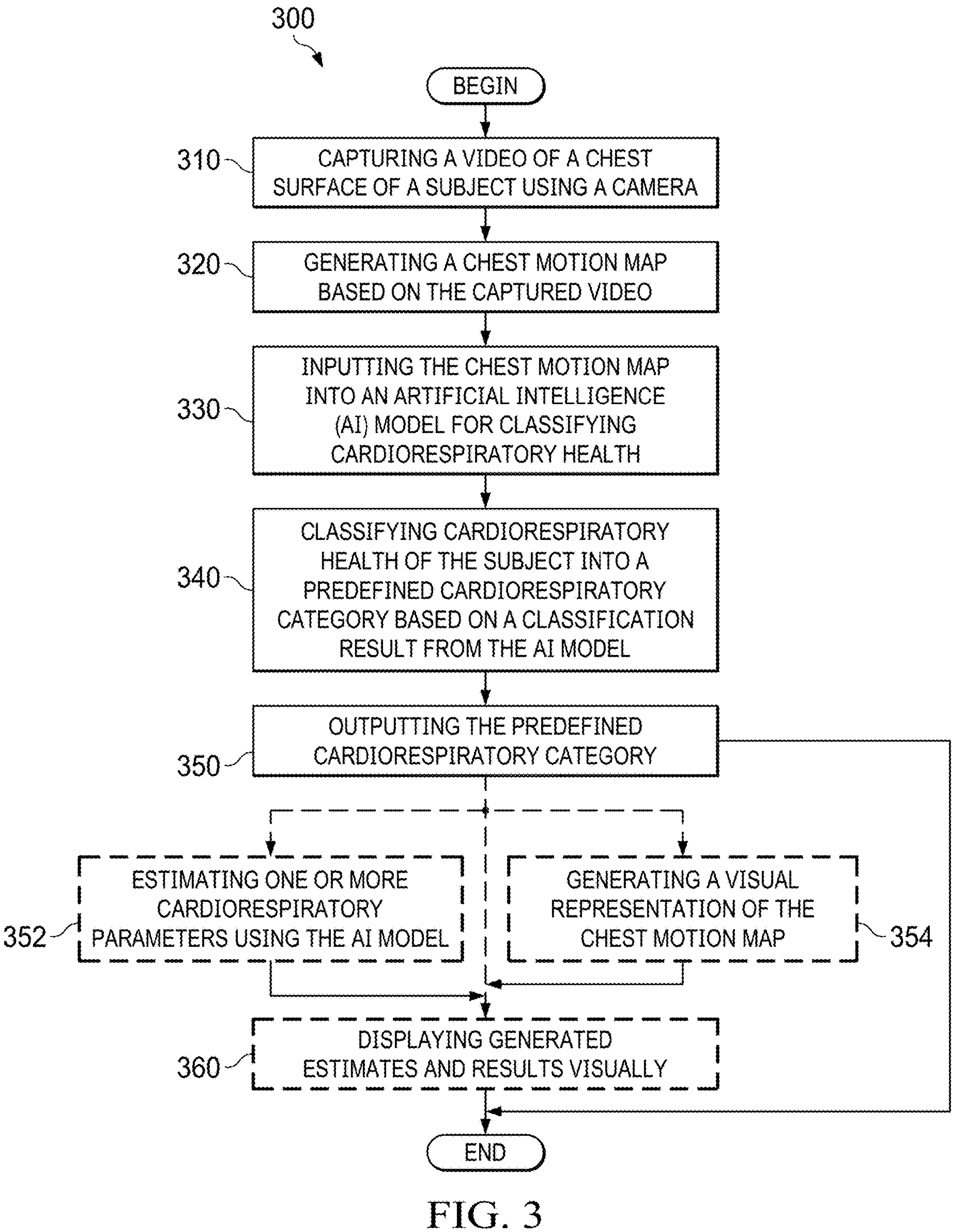
FIG. 3 is a flowchart of a method for cardiorespiratory health assessment in accordance with an embodiment of the disclosure.

FIG. 3 illustrates a method 300 for cardiorespiratory health assessment. The method 300 may be implemented using a vision-based cardiorespiratory monitor (e.g., the monitor 130) with an AI model (e.g., the deep learning model 150).

At step 310, the method 300 may include capturing a video of a chest surface of a subject using a camera. Step 310 in the method 300 may be similarly described as step 210 in the method 200 (supra). For instance, step 310 involves acquiring visual data that will be subsequently analyzed to extract information about the subject's cardiorespiratory function.

As discussed for step 210, in step 310, the camera used can be any suitable imaging device capable of recording video data. This may include but is not limited to, smartphone cameras, webcams, digital cameras, dedicated medical imaging cameras, or any other camera capable of capturing visual information of the chest surface. The camera should generally have sufficient resolution and frame rate to capture the subtle movements of the chest induced by cardiac and respiratory activity. The camera can be positioned in various ways to capture the chest surface. It can be handheld, mounted on a tripod or stand, or integrated into a wearable device. The optimal placement may depend on factors such as the subject's body position, the specific region of interest, and the desired field of view.

The video should generally focus on the chest area, as this is where the vibrations of interest are most prominent. However, the exact framing and field of view can be adjusted based on the specific goals of the monitoring session and the individual subject's anatomy. In some embodiments, the subject's skin may be prepared before recording to enhance the visibility of surface features and improve the accuracy of motion tracking. This may involve cleaning the skin, applying a light powder, or using markers to highlight specific anatomical landmarks.

The camera may capture a sequence of still images (frames) at a specific rate, generally measured in frames per second (fps). A higher frame rate may allow for more precise tracking of the rapid vibrations of the chest surface. For example, a minimum frame rate of 60 fps may be more useful to capture the full spectrum of cardiorespiratory activity. The resolution of the video refers to the number of pixels in each frame. Higher resolution may provide more detailed information about the chest surface, allowing for finer-grained analysis of the vibrations. The duration of the video capture may vary depending on the application and the desired level of detail in the analysis. A longer video duration may allow for capturing a wider range of cardiorespiratory events and variations over time.

At step 320, the method 300 includes generating a chest motion map based on the captured video. Step 320 in the method 300 may be similarly described as step 240 in the method 200 (discussed supra). For instance, step 310 involves transforming the visual information captured by the camera into a structured representation of the chest surface motion. These structured representations of the chest surface motion may serve as input for an AI model to assess cardiorespiratory health.

A substep in step 320 may involve tracking the movement of multiple points or regions on the chest surface throughout the video. This can be achieved using various techniques such as template matching or optical flow (as described in the step 220 discussion above). These techniques may analyze the changes in pixel positions between consecutive frames to estimate the displacement of each tracked point. Once the movement of each tracked point is determined, the method 320 calculates the corresponding motion vectors. These vectors represent the magnitude and direction of the displacement of each point in three-dimensional (3D) space. The motion vectors are then aggregated to create a dynamic 3D motion map of the chest surface. This map essentially represents a grid of vectors, where each vector corresponds to the motion of a specific point on the chest. The motion map captures the spatial and temporal dynamics of the chest surface vibrations induced by cardiorespiratory activity. The chest motion map can be represented in various formats, depending on the specific implementation and the requirements of the subsequent analysis. As discussed above, some representations include vector fields, displacement matrices, or spatiotemporal representations.

By analyzing the motion map, the AI model can extract relevant features, such as the amplitude, frequency, and direction of the vibrations at different locations on the chest. These features can then be used to classify cardiorespiratory health status, estimate physiological parameters, and detect potential abnormalities. The chest motion map may thus serve as a bridge between the raw video data and the clinical insights derived from it, allowing a non-invasive and more comprehensive assessment of cardiorespiratory health.

At step 330, the method 300 may involve inputting the chest motion map into an artificial intelligence (AI) model for classifying cardiorespiratory health. It should be noted that before step 330, a method for training the AI model may be performed. Such a method of training the AI model is discussed below as method 400, depicted in FIG. 4.

The use of AI, particularly deep learning, is enhancing the field of medical diagnosis and monitoring. By leveraging the power of AI, the vision-based cardiorespiratory monitor system may be able to analyze complex patterns in chest motion maps that may not be readily apparent to human observers. This may allow the method 300 (and associated systems) to identify subtle signs of cardiorespiratory dysfunction, potentially leading to earlier detection and intervention.

An AI model is a software algorithm designed to learn patterns and associations within data. In this context, the model may be trained to recognize specific patterns within chest motion maps that correlate with different cardiorespiratory health statuses. Various types of AI models can be employed, but deep learning models, particularly convolutional neural networks (CNNs), are generally used due to their ability to handle high-dimensional data like images and videos. CNNs can automatically learn hierarchical features from the motion maps, capturing subtle nuances that may be indicative of underlying conditions. The AI model may be trained on a dataset of chest motion maps labeled with corresponding cardiorespiratory health statuses. This training process may allow the model to learn the associations between specific motion patterns and different health conditions.

The chest motion map, generated from the video analysis as described in previous steps (e.g., step 320), is generally a numerical representation. This could be a 3D array of motion vectors, a series of 2D displacement maps, or any other format that captures the spatial and temporal dynamics of the chest surface vibrations. Before inputting the motion map into the AI model, it may undergo preprocessing steps such as normalization, feature extraction, or dimensionality reduction. These steps can help optimize the model's performance and improve the accuracy of the classification. The preprocessed motion map may then be fed into the input layer of the AI model. The model's architecture generally determines how this input is processed and transformed through subsequent layers to produce the final output.

The AI model generally uses the learned patterns from the training data to infer the cardiorespiratory health status of the subject based on the input motion map. This classification can be binary (e.g., healthy vs. unhealthy) or multi-class (e.g., normal, mild heart failure, severe heart failure). The AI model may also output probability scores associated with each possible classification, indicating the confidence level of the model in its prediction. An output of the AI model may be the classified cardiorespiratory health status, along with any associated probability scores. This information may then be presented to the user through the user interface (e.g., the user interface 190).

At step 340, the method 300 includes classifying cardiorespiratory health of the subject into a predefined cardiorespiratory category based on a classification result from the AI model. The classification result may indicate cardiorespiratory health status of the subject.

The ability to classify cardiorespiratory health may be a goal of a vision-based monitoring system. By leveraging the power of AI, the method 300 and associated systems may be able to automate this classification process, making it more accessible, objective, and scalable. This has the potential to improve the way cardiorespiratory health is assessed and managed, enabling early detection of diseases, remote monitoring of chronic conditions, and personalized treatment plans.

As discussed above, the AI model classifies the subject's cardiorespiratory health into predefined categories. These categories can be broad (e.g., "healthy" vs. "unhealthy") or more specific (e.g., "normal sinus rhythm," "atrial fibrillation," "heart failure," "asthma," or "comorbidity of asthma and heart failure"). The granularity of the categories may depend on the training data and the intended use of the system. The categories may be predefined based on medical knowledge and established diagnostic criteria. They may be based on existing classification systems (e.g., the New York Heart Association (NYHA) classification for heart failure) or developed specifically for the vision-based system. The method 300 and its associated systems are not limited to a fixed set of categories and may be adapted to different clinical settings or populations. For example, the categories could be tailored for specific age groups, risk factors, or disease conditions.

The AI model's classification result may be a label indicating the most likely cardiorespiratory category for the subject. The classification result may be based on the analysis of the chest motion map, which may serve as a proxy for the underlying cardiorespiratory activity. The AI model may be trained to recognize patterns in the motion map that correlate with different health statuses. The classification result may provide information for healthcare providers and patients that is used to guide further diagnostic testing, inform treatment decisions, and monitor disease progression.

Cardiorespiratory health status refers to the overall condition of the subject's cardiovascular and respiratory systems. This includes not only the presence or absence of specific diseases but also the functional capacity and efficiency of these systems. The AI model's classification result may be an indicator of the subject's cardiorespiratory health status. It may provide a snapshot assessment based on the captured video data. The classification result may not be a definitive diagnosis. It may be interpreted in conjunction with other clinical information and used to guide further investigation as needed.

In some embodiments, the model may also output a probability score associated with each category, reflecting the confidence level of the classification. Thus, instead of simply providing a single classification label, the model may also output a probability score for each predefined cardiorespiratory category. This probability score may quantify the model's confidence in its classification decision, adding a layer of nuance and interpretability to the results. A probability score is a numerical value between 0 and 1 (or 0% and 100%) that represents the likelihood or confidence that a particular event will occur. In this context, the probability score associated with each cardiorespiratory category may indicate the AI model's assessment of how likely it is that the subject belongs to that category.

Probability scores may be calculated using the SoftMax function, a mathematical function that converts a vector of real numbers into a probability distribution. The SoftMax function safeguards that the probability scores for all categories sum to 1. Interpretation: A higher probability score for a particular category may indicate that the AI model is more confident in its classification decision. For example, a probability score of 0.95 for the "healthy" category suggests that the model is 95% confident that the subject is healthy. Conversely, if the probability scores for multiple categories are similar, this may indicate that the model is less certain about the classification. This information can be valuable for healthcare providers, as it may warrant further investigation or the collection of additional data.

Probability scores may provide a more nuanced understanding of the AI model's classification decision, allowing users to assess the level of confidence associated with each category. This can be particularly useful in borderline cases where the distinction between categories is not clear-cut. Probability scores can aid healthcare providers in making informed decisions about further testing, diagnosis, and treatment. A high probability score for a specific condition may warrant immediate intervention, while a low probability score may suggest a wait-and-see approach or additional diagnostic tests. Probability scores can also be used to assess the calibration of the AI model, i.e., how well the predicted probabilities align with the observed frequencies of the different categories in the real world. This may aid in improving the reliability and validity of the model's predictions.

At step 350, the method 300 includes outputting the predefined cardiorespiratory category (e.g., via a graphical user interface (GUI)). The outputting of the predefined cardiorespiratory category may aid in translating the analysis performed by the AI model into actionable information. The way in which this information is presented may impact the user's understanding and response.

Using a GUI may provide a flexible and customizable platform for presenting the classification results. It may allow for the integration of various output formats, such as text, graphics, and numerical values, to cater to different user preferences and requirements. The GUI can also be designed to provide additional context and information, such as explanations of the different categories, potential causes of the identified condition, and recommendations for further action.

The output of the AI model's classification, which is the predefined cardiorespiratory category, can be presented in various formats such as textual, graphical, numerical, or a combination. A textual format may include a simple text label indicating the category (e.g., "Healthy," "Abnormal," "Heart Failure"). A graphical format may include a visual representation of the category, such as a color-coded bar, chart, or icon. A numerical format may include a numerical score or probability value associated with the category, indicating the confidence level of the classification. A combination of textual, graphical, and numerical formats may also be used to provide a more comprehensive or intuitive presentation of the results.

The output can be delivered through various channels, including a display, audio output, haptic feedback, or external devices. A display (e.g., display 180) may be able to show results on a device's screen, such as a smartphone, tablet, or computer monitor. In addition, the results may be converted into spoken words and delivered through the device's speaker or headphones. This can be particularly useful for visually impaired users. Further, a device may provide tactile (e.g., haptic) feedback, such as vibrations or pulsations, to alert the user of the classification results. Alternatively, the results can be transmitted to external devices, such as wearable displays, smartwatches, or medical monitors.

The GUI (e.g., user interface 190) may play a role in presenting the classification results to the user in a user-friendly and informative manner. It may provide a visual platform for displaying the results, along with additional context and information to aid interpretation. The GUI may be customized to meet the user's desires and the clinical setting. For example, it can be designed to highlight specific parameters, provide educational information about the classified condition, or offer recommendations for further action.

After step 350, the method 300 may end. Alternatively, step 350 may be followed by step 352, step 354, and/or step 360 before method 300 is concluded.

At step 352, the method 300 may include estimating one or more cardiorespiratory parameters using the AI model. Step 352 is an optional step emphasizing the method 300's ability to quantify specific physiological parameters related to the cardiovascular and respiratory systems. These parameters may provide additional insights into the underlying function and health of these heart and lung systems.

Cardiorespiratory parameters may encompass a range of physiological measures that reflect the function of the heart and lungs. Some examples of parameters that can be estimated using the AI model include heart rate (HR), heart rate variability (HRV), cardiac time intervals, cardiac parameters, blood pressure, timing of cardiac events, respiratory rate, and tidal volume. HR refers to the number of times the heart beats per minute. HRV refers to the variation in the time intervals between consecutive heartbeats. HRV is a measure of the autonomic nervous system's influence on the heart and can provide insights into stress, fitness, and overall health. Cardiac time intervals include measures such as the RR interval (time between consecutive heartbeats), left ventricular ejection time (LVET), pre-ejection period (PEP), and isovolumetric contraction and relaxation times. These intervals provide information about the timing and duration of different phases of the cardiac cycle. Cardiac parameters include measures such as stroke volume (the amount of blood pumped by the heart with each beat), cardiac output (the amount of blood pumped per minute), and ejection fraction (the percentage of blood pumped out of the heart with each beat). These parameters are indicators of overall cardiac function. Additionally, blood pressure, stroke work, cardiac work, and cardiac power can be estimated using the AI model based on correlations with other cardiorespiratory parameters. Further, the system can estimate the timing of specific cardiac events, such as the opening and closing of the heart valves. This information can be useful for diagnosing valvular diseases and assessing the overall coordination of the cardiac cycle. In addition, the system can estimate respiratory time intervals including inhalation time interval and exhalation time interval. Respiratory rate refers to the number of breaths taken per minute. Tidal volume refers to the amount of air inhaled and exhaled with each breath.

The AI model may estimate these parameters by analyzing the features extracted from the chest motion map. These features may include the vibrations' amplitude, frequency, and temporal patterns at different locations on the chest surface. The AI model may be trained on a dataset of chest motion maps with corresponding ground truth values for the cardiorespiratory parameters of interest. Such training allows the model to learn the relationships between the features in the motion map and the physiological parameters. Depending on the nature of the parameter, the AI model may perform either regression (predicting a continuous value) or classification (assigning a label to a discrete category). For example, heart rate estimation may be considered a regression task, while detecting arrhythmias may be considered a classification task.

The ability to estimate cardiorespiratory parameters non-invasively using a video-based system may improve healthcare by providing convenient, accessible, and low-cost techniques for monitoring patients with chronic conditions, assessing the effectiveness of treatments, and identifying early signs of disease progression. By leveraging the power of AI, the system can extract information from the subtle vibrations of the chest surface. This information can be used to provide personalized insights into cardiorespiratory health and guide clinical decision-making.

At step 354, the method 300 may include generating a visual representation of the chest motion map. Visualization of the chest motion map may allow the method 300 to transform complex numerical data into a more intuitive and interpretable format for both users and healthcare professionals. An objective of generating a visual representation of the chest motion map may be to facilitate understanding and analysis of the cardiorespiratory data. This visualization can reveal patterns, anomalies, and trends in the chest vibrations that may not be immediately apparent from the raw numerical data.

Visual representation may serve as a tool for qualitative assessment, communication and education, or research and development. For example, via visual representation, healthcare professionals may be able to assess the overall pattern of chest vibrations, identifying areas of abnormal movement or asymmetry that may warrant further investigation. The visual representation may be used to communicate the findings of the analysis to patients, helping them understand their cardiorespiratory health and the potential impact of various conditions or interventions. Researchers can use the visualizations to gain deeper insights into the mechanisms of cardiorespiratory function and to develop new diagnostic and therapeutic approaches.

The motion map can be visualized in various ways discussed above (e.g., heatmap, vector field, 3D surface plot, or animation), each offering a perspective on the underlying data. Generating a visual representation may involve mapping the numerical values in the motion map to visual elements, such as colors, arrows, or surface heights. This mapping can be done using various algorithms and techniques, such as color scaling, vector field visualization, or 3D rendering. The specific choice of visualization method may depend on the type of information to be conveyed, the user's preferences, and the display device's capabilities.

At step 360, the method 300 may include displaying generated estimates of cardiorespiratory parameters and motion map results visually. Step 360 may be used to present processed and visualized cardiorespiratory data to the user through a graphical user interface (GUI). This interaction may be useful for making data meaningful and actionable for both patients and healthcare providers. By presenting the data clearly, concisely, and visually appealingly, the GUI may empower users to understand their cardiorespiratory health and engage in informed decision-making. This can lead to early detection of abnormalities, timely intervention, and improved health outcomes.

The GUI (e.g., user interface 190) may be the primary interface between the user and the vision-based cardiorespiratory monitoring system. The GUI may provide a visual platform for displaying the analysis results, allow the user to interact with the data, and facilitate interpretation and decision-making. The GUI can be implemented in various forms, such as a mobile application on a smartphone or tablet, a web-based interface accessible through a browser, or a dedicated display integrated into the monitoring device. The GUI may include various elements to enhance user interaction and data visualization, such as a display area, controls, information panels, and alerts and notifications. A display area (e.g., display 180) is the main area where the visual representation of the chest motion map may be presented. Controls may include buttons, sliders, or other interactive elements that allow a user to control the monitoring process, adjust settings, and navigate through data. Information panels may include sections that display additional information, such as the classified cardiorespiratory health status, estimated parameters, and explanations of the results. Alerts and notifications may be visual or auditory cues that alert the user to potential abnormalities or events of interest.

The GUI may render the chest motion map in a visually intuitive format, such as a heatmap, vector field, or 3D surface plot. This may allow users to quickly grasp the overall pattern of chest vibrations and identify areas of interest. Additionally, the GUI may include interactive features that allow the user to manipulate the visualization, such as zooming in or out, panning across the map, or selecting specific regions for closer inspection. This may enhance users' ability to explore and analyze the data. Furthermore, the GUI may overlay additional information onto the motion map, such as anatomical landmarks, regions of interest, or numerical values representing the amplitude or frequency of vibrations. This can provide context and aid in interpretation.

In addition to the chest motion map, the GUI may also display the estimated cardiorespiratory parameters calculated by the AI model. This information can be presented in various formats, such as numerical values, graphs and charts, or comparative analysis. For example, the parameters can be displayed as numerical values alongside their corresponding units of measurement. Trends and variations in the parameters over time can be visualized using line graphs, bar charts, or other graphical representations. The GUI may allow for comparison of the estimated parameters with reference values or historical data, providing insights into the subject's health status and disease progression.

Figure 4:
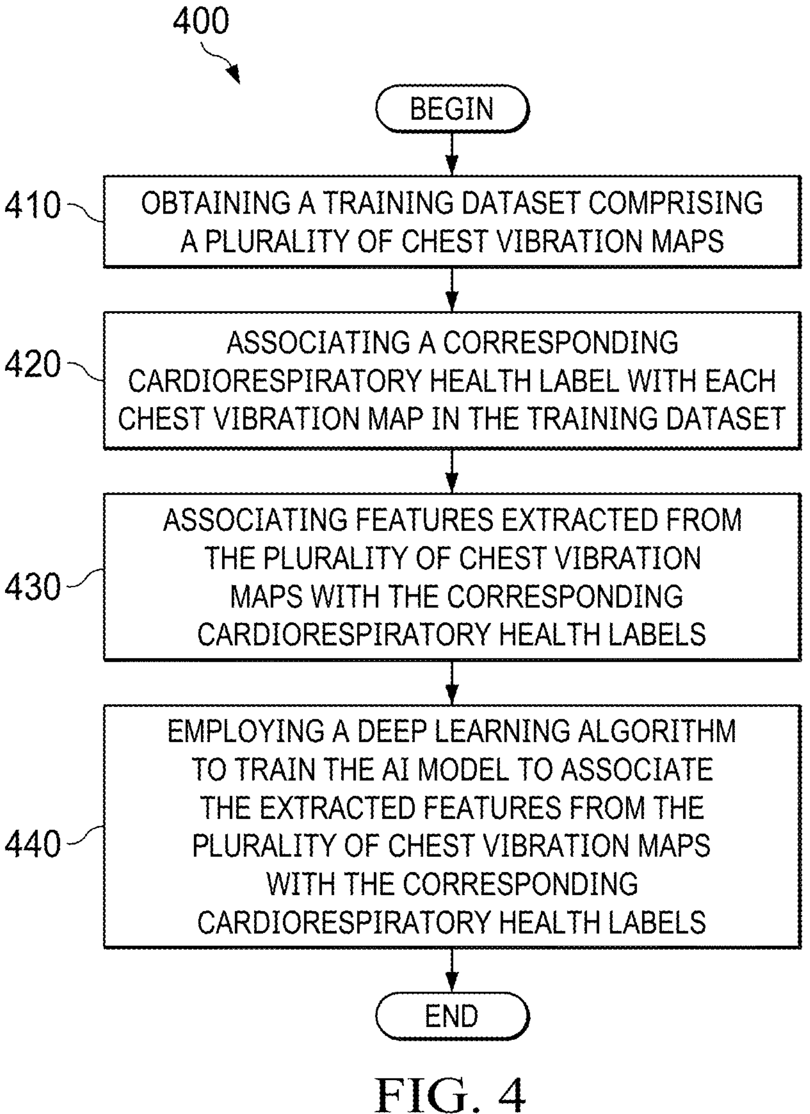
FIG. 4 is a flowchart of a method for training an AI model in accordance with an embodiment of the disclosure.

FIG. 4 illustrates a method 400 for training an AI model. The method 400 may be implemented as an intermediate step in the method 300 or separately. If implemented as an intermediate step in the method 300, the method 400 may be performed prior to step 330 in the method 300.

At step 410, the method 400 may include obtaining a training dataset comprising a plurality of chest vibration maps. The training dataset is a collection of examples used to teach the AI model how to associate specific patterns in chest vibration maps with corresponding cardiorespiratory health statuses. The model may learn from these examples by adjusting its internal parameters to minimize the error between its predictions and the ground truth labels in the dataset. The training dataset's quality, diversity, and size may impact the model's ability to learn patterns and make accurate predictions.

The training dataset comprises a plurality of chest vibration maps, each associated with a corresponding cardiorespiratory health label. These maps can be obtained from various sources, such as healthy subjects, patients with known conditions, and simulated data. For example, videos of healthy individuals undergoing the vision-based monitoring process may be used. These maps may provide examples of normal cardiorespiratory function and serve as a baseline for comparison. Additionally, videos of patients diagnosed with various cardiorespiratory conditions, such as heart failure, arrhythmias, or respiratory diseases, may be used. These maps may provide examples of abnormal patterns that the AI model may want to learn to recognize. Furthermore, synthetically generated chest vibration maps that mimic real-world data may be used. This can be useful for augmenting the training dataset and improving the model's robustness to variations in lighting, camera angles, and subject characteristics.

The training dataset may be diverse, encompassing various ages, genders, ethnicities, body types, and cardiorespiratory conditions. This diversity may help ensure that the AI model can generalize to new and unseen data, improving its accuracy and reliability in real-world applications. The size of the training dataset may also be considered. A larger dataset generally leads to better model performance, providing more examples for the model to learn from. However, the dataset may also be curated to improve its quality and relevance.

The process of obtaining the training dataset may involve collecting video recordings of the chest surface from a diverse group of subjects. This can be done in clinical settings, research studies, or even in the home environment using a smartphone or other camera-equipped device. Each video recording may then be processed to generate a chest vibration map, as previously described. The map may then be labeled (as discussed in more detail below) with the corresponding cardiorespiratory health status of the subject, which can be determined through clinical evaluation, diagnostic tests, or other means. In addition to labeling, the training dataset may be further annotated with additional information, such as the subject's demographics, medical history, and other relevant factors. This can help to improve the model's ability to personalize its predictions and identify potential risk factors.

At step 420, the method 400 may include associating a corresponding cardiorespiratory health label with each chest vibration map in the training dataset. Step 420 may involve assigning a label to each chest vibration map in the training dataset, indicating the corresponding cardiorespiratory health status of the subject from whom the map was derived.

Labels may serve as the target output that the AI model aims to predict. By associating each chest vibration map with a specific label, the model may learn to recognize the patterns in the map that correspond to different health statuses. The labeling scheme can be binary (e.g., "healthy" vs. "unhealthy") or multi-class (e.g., "normal," "mild heart failure," "severe heart failure," "arrhythmia"). The choice of labeling scheme may depend on the specific goals of the analysis and the desired level of granularity in the classification.

Labels can be determined through various methods, including clinical diagnosis, gold standard measurements, and expert review. For instance, a physician or healthcare professional can diagnose the subject's cardiorespiratory health status based on a comprehensive evaluation, including medical history, physical examination, and diagnostic tests. Alternatively, the labels can be based on established gold standard measurements for specific cardiorespiratory parameters, such as echocardiography for ejection fraction or spirometry for lung function. Furthermore, a panel of experts can review the chest vibration maps and assign labels based on their data interpretation and clinical expertise.

The association process may involve linking each chest vibration map in the training dataset to its corresponding cardiorespiratory health label. This can be done manually by a human annotator or automatically using a computer program. The associated data may be stored in a structured format, such as a table or database, where each row represents a single chest vibration map and its associated label. It may be worthwhile to consider the accuracy and consistency of the labels, as errors or inconsistencies in the labeling can negatively impact the performance of the AI model. This can be achieved through quality control measures, such as double-checking the labels by multiple annotators or using automated validation tools.

At step 430, the method 400 may include associating features extracted from the plurality of chest vibration maps with the corresponding cardiorespiratory health labels. Step 430 bridges the raw data (chest vibration maps) and the desired outcome (cardiorespiratory health labels) by identifying and quantifying the specific characteristics of the motion maps that are most relevant for determining health status.

An aim of feature extraction is to transform the raw chest vibration maps into a set of numerical values or vectors that represent the most salient and informative aspects of the data. These features are designed to capture the underlying patterns and variations in the vibrations that are associated with different cardiorespiratory conditions. The specific features that are extracted can vary depending on the nature of the data and the goals of the analysis. Some features used in cardiorespiratory monitoring include amplitude (e.g., the magnitude of the vibrations at different locations on the chest surface), frequency (e.g., the dominant frequencies present in the vibrations), temporal patterns (e.g., the timing and sequence of the vibrations throughout the cardiac and respiratory cycles), spatial distribution (e.g., the distribution of vibrations across different regions of the chest surface), and statistical measures (e.g., various statistical measures, such as mean, variance, and entropy, can be calculated from the vibration data to capture its overall characteristics). Features can be extracted using a variety of techniques, including signal processing (e.g., applying signal processing algorithms, such as Fourier transforms, wavelet transforms, or time-frequency analysis, to the raw vibration data), machine learning (e.g., using unsupervised learning algorithms, such as principal component analysis (PCA) or autoencoders, to identify and extract relevant features), and domain knowledge (e.g., incorporating expert knowledge about cardiorespiratory physiology to select features that are known to be associated with specific conditions).

The extracted features may then be associated with the corresponding cardiorespiratory health labels from the training dataset. This process may involve creating a mapping between the features and the labels, allowing the AI model to learn the relationships between them. Step 430 may also involve selecting the most relevant features and transforming or combining them to create new features that are more informative for the classification task. The associated features and labels may then be used to train the AI model. The model learns to recognize the patterns in the features that are predictive of the different cardiorespiratory health statuses.

At step 440, the method 400 may include employing a deep learning algorithm to train the AI model to associate the extracted features from the plurality of chest vibration maps with the corresponding cardiorespiratory health labels. By doing so, the method 400 may allow the AI model to learn patterns and relationships between the features and the cardiorespiratory health statuses.

The primary input to the deep learning algorithm is the training dataset, comprising pairs of chest vibration maps and their associated cardiorespiratory health labels. Each chest vibration map is a numerical representation of the spatiotemporal dynamics of chest surface motion, while the labels indicate the ground truth health status of the subject.

The deep learning algorithm works with a set of extracted features that have been derived from the maps. These features may include spatial features (e.g., amplitude, frequency, and directional information at different locations on the chest), temporal features (e.g., time-domain characteristics of the vibrations, such as heart rate variability (HRV) metrics, timing of cardiac events, and respiratory patterns), and statistical features (e.g., statistical measures like mean, variance, and entropy that summarize the overall characteristics of the vibrations).

As previously discussed, the deep learning algorithm analyzes the extracted features and their corresponding health labels to identify patterns and relationships. It learns to recognize which combinations of features are most indicative of different cardiorespiratory health statuses. Through an iterative training and validation process, the algorithm may adjust the internal parameters of the AI model to optimize its ability to predict health labels based on the input features more accurately. A goal is to train the model to generalize beyond the specific examples in the training dataset so that it can accurately classify new, unseen chest vibration maps.

The specific type of deep learning algorithm employed can vary, but some choices include CNNs, RNNs, LSTM networks, and transformers (as previously discussed). The primary output of the deep learning algorithm is a trained AI model that can associate extracted features from chest vibration maps with their corresponding cardiorespiratory health labels. The algorithm also may produce a set of enhanced model parameters, such as weights and biases, that define the internal structure and function of the AI model.

It may be beneficial that the training dataset is not limited to a small or homogenous group of individuals. Instead, the training dataset may include chest vibration maps generated by a plurality of subjects with a plurality of different diverse cardiorespiratory conditions. This may mean chest vibration maps from a diverse population with varying ages, genders, ethnicities, body types, and health statuses. This diversity may help ensure that the AI model learns to recognize patterns of chest vibrations that are representative of the broader population. A model trained on a narrow or biased dataset may perform poorly when applied to individuals with different characteristics.

Furthermore, using a plurality of different diverse cardiorespiratory conditions may emphasize a benefit of including chest vibration maps from subjects with a wide range of health conditions, not just healthy individuals. This may allow the AI model to learn to distinguish between normal and abnormal patterns of chest vibrations and to identify specific conditions based on the observed features. Including diverse cardiorespiratory conditions in the training dataset may thus be useful for improving the diagnostic accuracy of the AI model. A model trained only on healthy subjects may not be able to identify abnormal patterns or diagnose specific conditions.

The training dataset may include chest vibration maps from subjects with various cardiorespiratory conditions, such as individuals who are healthy, individuals with cardiovascular diseases, individuals with respiratory diseases, or individuals with other conditions. Healthy individuals may provide a baseline for normal cardiorespiratory function and help the AI model learn to recognize healthy patterns. Cardiovascular diseases may include conditions like heart failure, arrhythmias (e.g., atrial fibrillation), valvular diseases, and coronary artery disease. Respiratory diseases may include conditions like asthma, chronic obstructive pulmonary disease (COPD), pneumonia, and sleep apnea. The dataset may also include subjects with other conditions that can affect cardiorespiratory function, such as obesity, diabetes, and hypertension.

By training on a diverse dataset, the AI model can learn to generalize from the specific examples it has seen and make more accurate predictions on new, unseen data. This improves the model's ability to identify subtle variations in chest vibrations that may be indicative of different health conditions, leading to more reliable and informative cardiorespiratory assessments.

Figure 5:
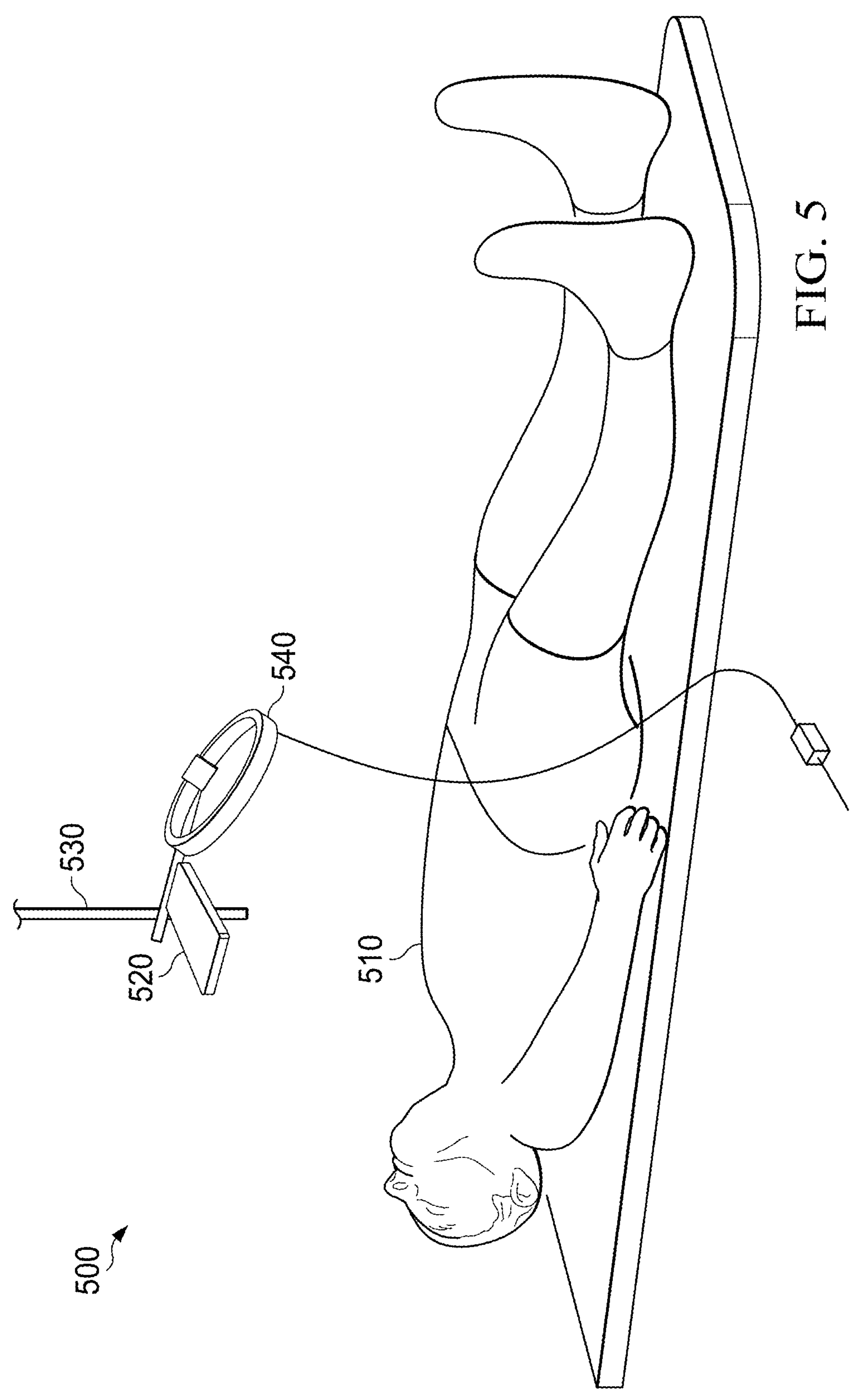
FIG. 5 illustrates an exemplary setup for capturing video data of a chest surface for cardiorespiratory monitoring in accordance with an embodiment of the disclosure.

FIG. 5 illustrates an exemplary setup 500 for capturing video data of the chest surface using a camera for the purpose of cardiorespiratory monitoring according to an embodiment of the disclosure. The exemplary setup 500 includes a subject 510, a camera 520, a holder 530, and a light source 540.

The subject 510 may be a person lying in a supine position (e.g., lying horizontally with the face and torso facing up) on a flat surface. The supine position may be chosen because it may provide a stable and consistent resting position for the subject, reducing motion artifacts and facilitating improved measurement of chest vibrations.

The camera 520 may be any type of suitable device (e.g., a smartphone equipped with a camera) positioned above the subject 510's chest. The camera 520 is a component of the system responsible for capturing video data of the chest surface vibrations of the subject 510. The camera may have a frame rate sufficient to accurately capture the subtle and rapid movements associated with cardiorespiratory activity. The camera 520 may be a standard smartphone camera or a dedicated medical imaging camera with additional features such as high resolution, autofocus, and image stabilization.

The holder 530 may be used to position the camera above the subject 510's chest. The holder 530 can be a tripod, a stand, or any other suitable support structure that ensures stable and consistent image framing. The holder 530 may be adjustable to accommodate subjects of different sizes and body positions.

The light source 540 provides illumination of the chest surface of the subject 510. The light source 540 may be uniform and controlled illumination of the chest surface, reducing shadows and improving image quality. This may aid in accurate motion tracking and analysis of the video data. A ring light configuration, as shown in FIG. 5, may provide even illumination from many angles, reducing glare and the impact of ambient lighting conditions.

The specific components and configuration shown in FIG. 5 are exemplary and can be modified based on the specific requirements of the application. For instance, the camera 520 may be mounted on a wearable device for continuous monitoring in ambulatory settings, or multiple cameras can be used to capture a wider field of view or provide 3D reconstruction of the chest surface.

Figure 6:
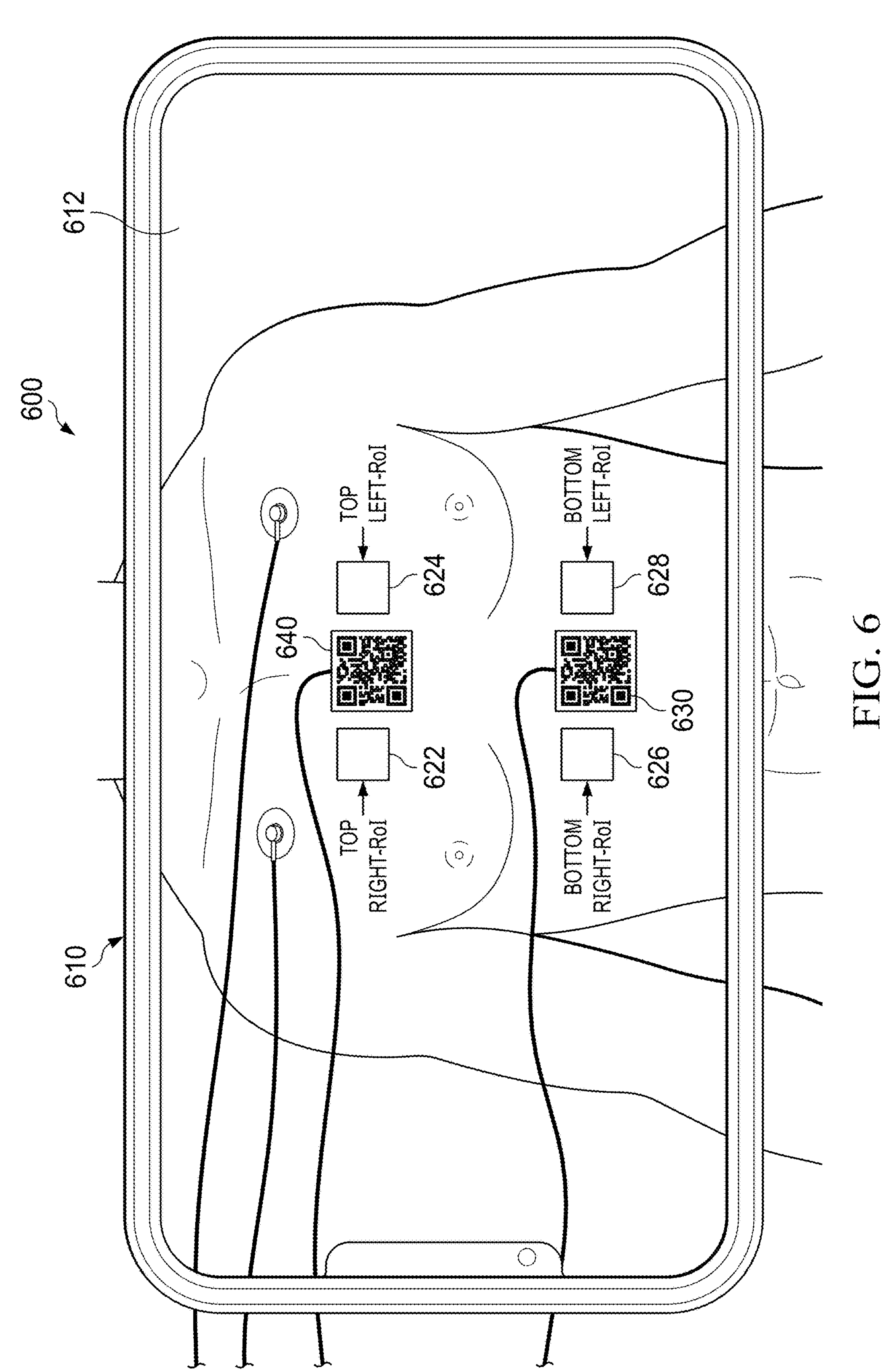
FIG. 6 illustrates a topical view of an exemplary device during a monitoring process in accordance with an embodiment of the disclosure.

FIG. 6 illustrates a topical view 600 of a smartphone 610 with a screen 612 during an exemplary vision-based cardiorespiratory monitoring process, showcasing several elements, in accordance with embodiments described herein. The central part of the screen 612 displays a live video feed of the subject's chest. This may allow the user to appropriately position and frame the chest of a subject (e.g., subject 510) within the camera's (e.g., camera 520) view.

In the topical view 600 example, four distinct regions of interest (ROIs) are highlighted on the chest surface. These are top right ROI 622, top left ROI 624, bottom right ROI 626, and bottom left ROI 628. These ROIs are exemplary and may correspond to anatomical locations that may be relevant for cardiorespiratory assessment. The top right ROI 622 and top left ROI 624 may capture cardiorespiratory vibrations from the upper chest, while the bottom right ROI 626 and bottom left ROI 628 may capture cardiorespiratory vibrations from the lower chest.

Patterned stickers 630, such as quick response (QR) codes, may be also placed on the chest. Patterned stickers 630 may be used for various purposes, such as camera calibration, data association, system initialization, and providing high contrast regions for more accurate tracking of chest motion. For camera calibration, patterned stickers 630 may assist in calibrating the camera's position and orientation relative to the subject's chest. This may improve accurate motion tracking and subsequent analysis of vibrations. For data association, patterned stickers 630 may be used to associate the video data with specific anatomical locations, facilitating region-specific analysis of the vibrations. For system initialization, scanning patterned stickers 630 may initiate the monitoring process and trigger the software to start analyzing the video data. Patterned stickers 630 can also serve as high contrast regions to facilitate chest motion tracking.

An accelerometer 640, a sensor that measures acceleration, is shown attached to the chest. While not necessarily part of the vision-based system, the accelerometer 640 data can be used for comparison and validation of the vision-based measurements.

The screen 612 may also include elements of the graphical user interface (GUI) (e.g., user interface 190), such as buttons or icons for starting/stopping the recording, adjusting camera settings, and accessing additional features or information. In some embodiments, the screen 612 may overlay real-time data onto the video feed, such as heart rate or respiratory rate estimates derived from the vision-based analysis. This may provide instantaneous feedback to a user and can aid in assessing the subject's cardiorespiratory status.

FIG. 6 demonstrates a practical application of the vision-based cardiorespiratory monitoring system. It highlights the interface, the use of visual cues (e.g., ROIs and patterned stickers) to guide a user, and the potential integration with other sensor data. Topical view 600 visually represents how the system can be used in real-world scenarios, possibly making it easier for users and healthcare providers to understand the system's operation and potential benefits.

The specific layout and design of the display can be customized based on the device and intended use case. The elements shown in FIG. 6 are exemplary and can be modified or augmented to suit the application's specific requirements.

Figure 7:
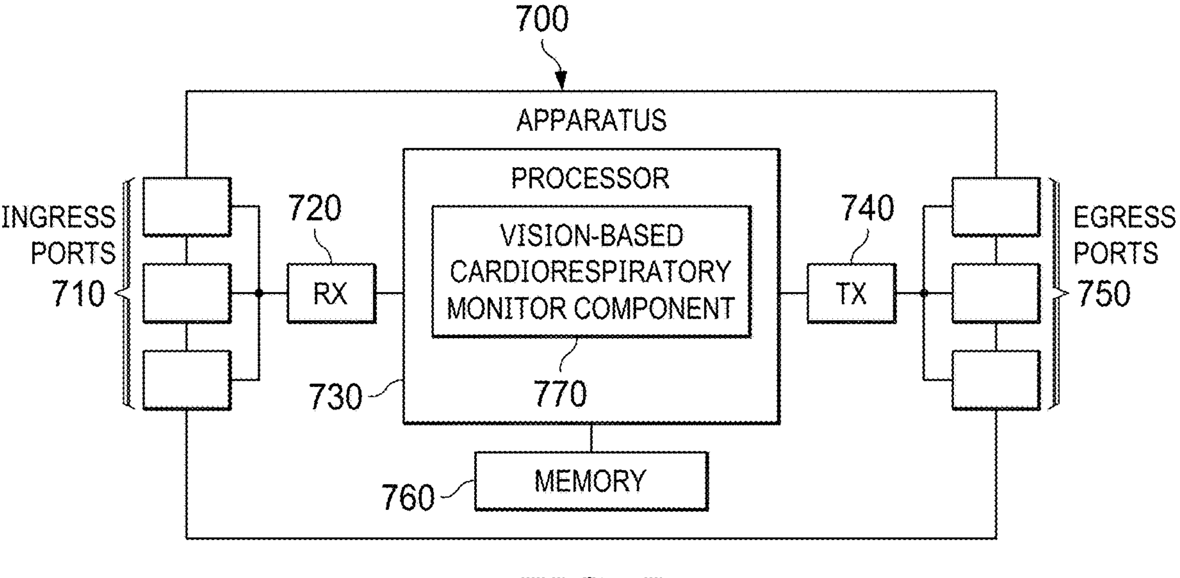
FIG. 7 is a schematic diagram of an example vision-based cardiorespiratory monitor in accordance with an embodiment of the disclosure.

FIG. 7 is a schematic diagram of an apparatus 700 according to an embodiment of the disclosure. The apparatus 700 may implement the disclosed embodiments. The apparatus 700 comprises ingress ports 710 and a receiver unit (RX) 720 to receive data; a processor 730, or logic unit, baseband unit, or central processing unit (CPU), to process the data; a transmitter unit (TX) 740 and egress ports 750 to transmit the data; and a memory 760 to store the data. The apparatus 700 may also comprise optical-to-electrical (OE) components, electrical-to-optical (EO) components, or radio frequency (RF) components coupled to the ingress ports 710, the RX 720, the TX 740, and the egress ports 750 to provide ingress or egress of optical signals, electrical signals, or RF signals.

The processor 730 is any combination of hardware, middleware, firmware, or software. The processor 730 comprises any combination of one or more CPU chips, graphical processing unit (GPU) chips, cores, field-programmable gate array (FPGAs), application-specific integrated circuit (ASICs), or digital signal processor (DSPs). The processor 730 communicates with the ingress ports 710, the RX 720, the TX 740, the egress ports 750, and the memory 760. The processor 730 comprises a vision-based cardiorespiratory monitor component 770, which implements the disclosed embodiments. The inclusion of the vision-based cardiorespiratory monitor component 770 therefore provides a substantial improvement to the functionality of the apparatus 700 and effects a transformation of the apparatus 700 to a different state. Alternatively, the memory 760 stores the vision-based cardiorespiratory monitor component 770 as instructions, and the processor 730 executes those instructions.

The memory 760 comprises any combination of disks, tape drives, or solid-state drives. The apparatus 700 may use the memory 760 as an overflow data storage device to store programs when the apparatus 700 selects those programs for execution and to store instructions and data that the apparatus 700 reads during execution of those programs. The memory 760 may be volatile or non-volatile and may be any combination of read-only memory (ROM), random-access memory (RAM), ternary content-addressable memory (TCAM), or static RAM (SRAM).

A computer program product may comprise computer-executable instructions that are stored on a computer-readable medium and that, when executed by a processor, cause an apparatus to perform any of the embodiments. The non-transitory medium may be the memory 760, the processor may be the processor 730, and the apparatus may be the apparatus 700.

While several embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the disclosure. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

Thus, the preceding discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the preceding description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form, and some details of conventional elements may not be shown in the interest of clarity and conciseness.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

In the preceding discussion and the claims, the terms "including" and "comprising" are used in an open-ended fashion and thus should be interpreted to mean "including, but not limited to . . . " Also, the term "couple" or "couples" is intended to mean either an indirect or direct connection. Thus, if a first device couples to a second device, that connection may be through a direct engagement between the two devices or through an indirect connection established via other devices, components, nodes, and connections. In addition, as used herein, the terms "axial" and "axially" generally mean along or parallel to a particular axis (e.g., a central axis of a body or a port), while the terms "radial" and "radially" generally mean perpendicular to a particular axis. For instance, an axial distance refers to a distance measured along or parallel to the axis, and a radial distance means a distance measured perpendicular to the axis. As used herein, the terms "approximately," "about," "substantially," and the like mean within 10% (i.e., plus or minus 10%) of the recited value. Thus, for example, a recited angle of "about 80 degrees" refers to an angle ranging from 72 degrees to 88 degrees.

What is claimed is:

1. A method, comprising:

capturing a video of a chest region of a subject using a camera, wherein the video comprises a plurality of consecutive frames;

defining, in an initial frame of the plurality of consecutive frames, a region of interest ROI), wherein the ROI comprises a group of pixels in the initial frame;

for each subsequent frame of the plurality of consecutive frames:

comparing a plurality of first pixel groups within the subsequent frame to the ROI;

based on comparing the plurality of first pixel groups to the ROI, determining that a first pixel group of the plurality of first pixel groups is more similar to the ROI than remaining pixel groups of the plurality of first pixel groups; and designating the ROI or the first pixel group as the ROI;

determining multi-dimensional movement of the ROI between the plurality of consecutive frames; and constructing a motion map of the chest region based on the multi-dimensional movements of the ROI, wherein the motion map represents vibrations of the chest region and indicates movement of each area of the chest region corresponding to the ROI in multiple dimensions with respect to time.

2. The method of claim 1, wherein the multiple dimensions include axial vibrations and rotational vibrations in one or more of x, y, and z dimensions.

3. The method of claim 1, further comprising applying a filtering algorithm to the motion map to reduce noise.

4. The method of claim 1, further comprising generating a visual representation of the motion map.

5. The method of claim 1, wherein the tracking of the plurality of pixel groups comprises a template matching technique or a Farneback optical flow technique.

6. The method of claim 1, wherein the multiple dimensions include x, y, and z dimensions.

7. The method of claim 1, wherein comparing the plurality of first pixel groups to the ROI comprises determining an amount of warping between the plurality of first pixel groups and the ROI.

8. A method, comprising:

capturing a video of a chest region of a subject using a camera;

defining, in an initial frame of the video, a region of interest (ROI), wherein the ROI comprises a group of pixels in the initial frame;

for each subsequent frame of the video:

comparing a plurality of first pixel groups within the subsequent frame to the ROI;

based on comparing the plurality of first pixel groups to the ROI, determining that a first pixel group of the plurality of first pixel groups is more similar to the ROI than remaining pixel groups of the plurality of first pixel groups; and designating the ROI or the first pixel group as the ROI;

generating a chest motion map based on movement of the ROI, wherein the chest motion map indicates movement of each area of the chest region corresponding to the ROI in multiple dimensions with respect to time;

inputting the chest motion map into an artificial intelligence (AI) model for classifying cardiorespiratory health; and classifying cardiorespiratory health of the subject into a predefined cardiorespiratory category based on a classification result from the AI model, wherein the classification result indicates cardiorespiratory health status of the subject.

9. The method of claim 8, further comprising:

obtaining a training dataset comprising a plurality of chest vibration maps;

associating a corresponding cardiorespiratory health label with each chest vibration map in the training dataset;

associating features extracted from the plurality of chest vibration maps with the corresponding cardiorespiratory health labels; and employing a deep learning algorithm to train the AI model to associate the extracted features from the plurality of chest vibration maps with the corresponding cardiorespiratory health labels, allowing the AI model to learn patterns and relationships between the features and cardiorespiratory health statuses.

10. The method of claim 9, wherein the training dataset comprises chest vibration maps generated from a plurality of subjects with a plurality of different diverse cardiorespiratory conditions.

11. The method of claim 8, further comprising estimating one or more cardiorespiratory parameters using the AI model.

12. The method of claim 8, further comprising generating a visual representation of the chest motion map and displaying the visual representation of the chest motion map on a user interface.

13. The method of claim 8, wherein the AI model outputs a probability score associated with each of the predefined cardiorespiratory category.

14. An apparatus, comprising:

a camera configured to capture a video of a chest region of a subject; and a processing unit coupled to the camera, the processing unit configured to:

define, in an initial frame of the video, a region of interest (ROI), wherein the ROI comprises a group of pixels in the initial frame;

for each subsequent frame of the video:

compare a plurality of first pixel groups within the subsequent frame to the ROI;

based on comparing the plurality of first pixel groups to the ROI, determine that a first pixel group of the plurality of first pixel groups is more similar to the ROI than remaining pixel groups of the plurality of first pixel groups; and designate the ROI or the first pixel group as the ROI;

determine multi-dimensional movement of the ROI between consecutive frames of the video;

construct a motion map of the chest region based on the multi-dimensional movements of the ROI, wherein the motion map represents vibrations of the chest region and indicates movement of each area of the chest region corresponding to the ROI in multiple dimensions with respect to time;

generate a chest vibration map based on the motion map; and input the chest vibration map into an artificial intelligence (AI) model for cardiorespiratory health assessment.

15. The apparatus of claim 14, further comprising a display configured to visually output the motion map.

16. The apparatus of claim 14, further comprising a display configured to visually output a classification result from the AI model.

17. The apparatus of claim 14, wherein the processing unit is further configured to estimate one or more cardiorespiratory parameters using the AI model.

18. The apparatus of claim 14, further comprising a light source configured to provide illumination on the chest region of the subject during video capture.

19. The apparatus of claim 14, further comprising a communication system for transmitting information.

20. The apparatus of claim 14, wherein the processing unit is configured to connect to a wearable device for continuous monitoring of cardiorespiratory health.

* * * * *